United States Patent
Slouka et al.

(10) Patent No.: US 10,247,720 B2
(45) Date of Patent: Apr. 2, 2019

(54) INTEGRATED MEMBRANE SENSOR FOR RAPID MOLECULAR DETECTION

(71) Applicant: University of Notre Dame du Lac, Notre Dame, IN (US)

(72) Inventors: Zdenek Slouka, South Bend, IN (US); Satyajyoti Senapati, Mishawaka, IN (US); Sunny S. Shah, Mishawaka, IN (US); Hsueh-Chia Chang, Granger, IN (US)

(73) Assignee: UNIVERSITY OF NOTRE DAME DU LAC, Notre Dame, IN (US)

(*) Notice: Subject to any disclaimer, the term of this patent is extended or adjusted under 35 U.S.C. 154(b) by 107 days.

(21) Appl. No.: 15/312,585

(22) PCT Filed: May 21, 2015

(86) PCT No.: PCT/US2015/032079
§ 371 (c)(1),
(2) Date: Nov. 18, 2016

(87) PCT Pub. No.: WO2015/179712
PCT Pub. Date: Nov. 26, 2015

(65) Prior Publication Data
US 2017/0108485 A1 Apr. 20, 2017

Related U.S. Application Data

(60) Provisional application No. 62/002,098, filed on May 22, 2014, provisional application No. 62/051,606, (Continued)

(51) Int. Cl.
*G01N 27/447* (2006.01)
*G01N 27/333* (2006.01)
(Continued)

(52) U.S. Cl.
CPC .. *G01N 33/48721* (2013.01); *B01L 3/502753* (2013.01); *G01N 27/3276* (2013.01);
(Continued)

(58) Field of Classification Search
CPC ..... B01L 2300/0645; B01L 2300/0681; B01L 2400/0418; B01L 2400/0421;
(Continued)

(56) References Cited

U.S. PATENT DOCUMENTS 4,661,224 A 4/1987 Goldstein et al.
6,893,816 B1 5/2005 Beattie
(Continued)

FOREIGN PATENT DOCUMENTS

| WO | WO 2005/078139 A2 | 8/2005 |
| WO | WO 2012/020308 A2 | 2/2012 |
| WO | WO 2013/074793 A1 | 5/2013 |

OTHER PUBLICATIONS

Slouka et al, "Microfluidic Systems with Ion-Selective Membranes", 2014, Annual Review of Analytical Chemistry, vol. 7, pp. 317-335. (Year: 2014).*

(Continued)

*Primary Examiner* — Jennifer Wecker
(74) *Attorney, Agent, or Firm* — Knobbe Martens Olson & Bear LLP

(57) ABSTRACT

Disclosed are methods, compositions, and devices for an integrated, heterogeneous ion-exchange membrane-based plastic microfluidic biochip platform that can be used to detect multiple diagnostic markers present in real samples. Its various components can be easily integrated in a modular fashion for different applications. Automated control allows sequential and dynamic activation of different components on the chip. The integrated platform consists of three units and is designed to execute the following functions: (i)
(Continued)

separation of the target biomolecules from the real sample, (ii) localizing and concentrating the targeted molecules at a specific location in the microfluidic chip, and (iii) detection of the targeted molecules using hybridization/docking events against a complementary ssDNA oligoprobe sequence or a specific antibody.

7 Claims, 31 Drawing Sheets

Related U.S. Application Data filed on Sep. 17, 2014, provisional application No. 62/075,647, filed on Nov. 5, 2014.

(51) Int. Cl.
| | | |
|---|---|---|
| *G01N 33/487* | (2006.01) | |
| *B01L 3/00* | (2006.01) | |
| *G01N 27/327* | (2006.01) | |
| *G01N 1/40* | (2006.01) | |

(52) U.S. Cl.
CPC . *G01N 27/44743* (2013.01); *G01N 27/44791* (2013.01); *B01L 2300/0645* (2013.01); *B01L 2300/0681* (2013.01); *B01L 2400/0415* (2013.01); *B01L 2400/0418* (2013.01); *B01L 2400/0421* (2013.01); *B01L 2400/0487* (2013.01); *G01N 2001/4011* (2013.01)

(58) Field of Classification Search
CPC ....... B01L 2400/0487; B01L 3/502753; B01L 2400/0415; G01N 27/44743; G01N 27/44791; G01N 33/48721; G01N 2001/4011; G01N 27/3276
See application file for complete search history.

(56) References Cited

U.S. PATENT DOCUMENTS

| | | | | |
|---|---|---|---|---|
| 2008/0257811 | A1 | 10/2008 | Peterman et al. | |
| 2009/0242406 | A1* | 10/2009 | Han ................ | B01L 3/502707 204/520 |
| 2013/0068632 | A1* | 3/2013 | Chang ............. | G01N 27/4146 205/780.5 |

OTHER PUBLICATIONS

Baeumner, Anal Bioanal Chem. Sep. 2004;380(1):15-23. A rapid biosensor for viable B. anthracis spores.
Bakker, Anal Chem. Jun. 15, 2006;78(12):3965-84. Electrochemical sensors.
Basuray, ACS Nano. Jul. 28, 2009;3(7):1823-30. Shear and AC Field Enhanced Carbon Nanotube Impedance Assay for Rapid, Sensitive, and Mismatch-Discriminating DNA Hybridization.
Bhatt, Nature. Apr. 25, 2013;496(7446):504-7. The global distribution and burden of dengue.
Cheng, Lab Chip. Apr. 7, 2010;10(7):828-31. A rapid field-use assay for mismatch number and location of hybridized DNAs.
Concepcion et al., Cancer J., 18(3):262-7 (2012).
Fritz et al., "Electronic detection of DNA by its intrinsic molecular charge," PNAS, Oct. 29, 2012, vol. 99, No. 22, pp. 14142-14146.
Gao et al., Cancer, 119: 72-80 (2013).
Gubler, Am J Trop Med Hyg. May 2012;86(5):743-4. doi: 10.4269/ajtmh.2012.12-0157. The economic burden of dengue.
Gunasekharan V, Laimins La., J Virol. 87(10):6037-43 (2013).
Hui et al., Clin Cancer Res, 19: 2154-2162 (2013).
International Search Report dated Aug. 21, 2015 for International Application No. PCT/US2015/032079, filed Aug. 21, 2015.
International Search Report, dated Feb. 6, 2015, received in corresponding International Patent Application No. PCT/US2014/51692.
Johannsen E, Lambert P F., Virology, 445(1-2):205-12 (2013).
Kao, J Microbiol Immunol Infect. Feb. 2005;38(1):5-16. Laboratory diagnosis of dengue virus infection: current and future perspectives in clinical diagnosis and public health.
Khoury et al., J Virol., 87(16): 8916-26 (2013).
Kyle, Annu Rev Microbiol. 2008;62:71-92. Global spread and persistence of dengue.
Lajer et al., Br J Cancer, 104(5): 830-40 (2011).
Lajer et al., Br J Cancer, 106:1526-1534 (2012).
Lal et al., PLoS Genetics 7(11): e1002363 (2011).
Lampman, J Am Mosq Control Assoc. Mar. 2006;22(1):76-86. A comparison of two West Nile virus detection assays (TaqMan reverse transcriptase polymerase chain reaction and VecTest antigen assay) during three consecutive outbreaks in northern Illinois.
Linssen, J Clin Microbiol. Apr. 2000;38(4):1527-35. Development of reverse transcription-PCR assays specific for detection of equine encephalitis viruses.
Liu et al., "Capillar-valve-based fabrication of ion-selective membrane junction for electrokinetic sample preconcentration in PDMS chip," Lab Chip, 2010, 10, 1485-1490.
Lyford-Pike et al., Cancer Res., 73(6): 1733-41 (2013).
Mangold, Pediatr Emerg Care. May 2013;29(5):665-9. A review of dengue fever: a resurging tropical disease.
Miller et al., Biochem J. 443, 339-353 (2012).
Niyas, Virol J. Aug. 13, 2010;7:189. Molecular characterization of Chikungunya virus isolates from clinical samples and adult Aedes albopictus mosquitoes emerged from larvae from Kerala, South India.
Nkodo, Electrophoresis. Aug. 2001;22(12):2424-32. Diffusion coefficient of DNA molecules during free solution electrophoresis.
Office Action dated Aug. 1, 2018 for European Application No. 15795795.2, filed Dec. 5, 2016.
Pabbaraju, J Clin Microbiol. Nov. 2009;47(11):3454-60. Design and validation of real-time reverse transcription-PCR assays for detection of pandemic (H1N1) 2009 virus.
Park et al., "An approach to fouling characterization of an ion-exchange membrane using current-voltage relation and electrical impedance spectroscopy," J. Coll. And Interface Sci., 294, 2006, 129-138.
Peltier, H J, Latham, G J, RNA, 14(5):844-52 (2008).
Petrocca et al., Cancer Cell., 13(3): 272-86 (2008).
Philippidou et al, Cancer Res., 70(10):4163-73 (2010).
Poloni, Virol J. Jan. 27, 2010;7:22. Detection of dengue virus in saliva and urine by real time RT-PCR.
Rampias et al., Ann Oncol., 24(8): 2124-31 (2013).
Sando, J Am Chem Soc. Aug. 21, 2002;124(33):9686-7. Imaging of RNA in bacteria with self-ligating quenched probes.
Saxena, Trans R Soc Trop Med Hyg. Apr. 2009;103(4):403-6. Evaluation of reverse-transcriptase PCR as a diagnostic tool to confirm Japanese encephalitis virus infection.
Schetter et al., JAMA., 299(4): 425-36 (2008).
Schultz et al., JAMA., 311(4):392-404 (2014).
Senapati et al. A Nanomembrane-Based Nucleic Acid Sensing Platform for Portable Diagnostics. Springer Berlin Heidelberg. Apr. 27, 2011.
Senapati et al. An ion-exchange nanomembrane sensor for detection of nucleic acids using a surface charge inversion phenomenon. Biosensors and Bioelectronics 60. Apr. 13, 2014.
Senapati, Biomicrofluidics. May 4, 2009;3(2):22407. Rapid on-chip genetic detection microfluidic platform for real world applications.
Slouka et al. Charge Inversion, Water Splitting, and Vortex Suppression Due to DNA Sorption on Ion-Selective Membranes and Their Ion-Current Signatures. Langmuir. 2013.
Slouka et al. Microfluidic Systems with Ion-Selective Membranes. Annual Review of Analytical Chemistry. Apr. 14, 2014, pp. 317-335, 7:1.
Socher, Angew Chem Int Ed Engl. 2008;47(49):9555-9. Low-noise stemless PNA beacons for sensitive DNA and RNA detection.
Sosnowski, Proc Natl Acad Sci U S A. Feb. 18, 1997;94(4):1119-23. Rapid determination of single base mismatch mutations in DNA hybrids by direct electric field control.

(56) References Cited

OTHER PUBLICATIONS

Suni, Angew Chem Int Ed Engl. 2008;47(39):7442-5. Selective surface patterning with an electric discharge in the fabrication of microfluidic structures.
Syrjanen S., J Clin Pathol., 57(5):449-55 (2004).
Tantawichien, Paediatr Int Child Health. May 2012;32 Suppl 1:22-7. Dengue fever and dengue haemorrhagic fever in adolescents and adults.
Ukpo et al., Head Neck Pathol., 6(1): 38-47 (2012).
Umezawa, Anal Chem. Sep. 1, 2004;76(17):321A-326A. Ion channel based on artificial receptors.
Ventura et al., Cell, 132(5):875-86 (2008).
Wald et al., Head Neck, 33(4):504-12 (2011).
Weidmann, J Clin Virol. Jul. 2010;48(3):187-92. Improved LNA probe-based assay for the detection of African and South American yellow fever virus strains.
Zhang, Langmuir. Oct. 10, 2006;22(21):9062-6. Measurements of interface stress of silicon dioxide in contact with water-phenol mixtures by bending of microcantilevers.
Zhuang et al., EMBO J 31: 3513-3523 (2012).

\* cited by examiner

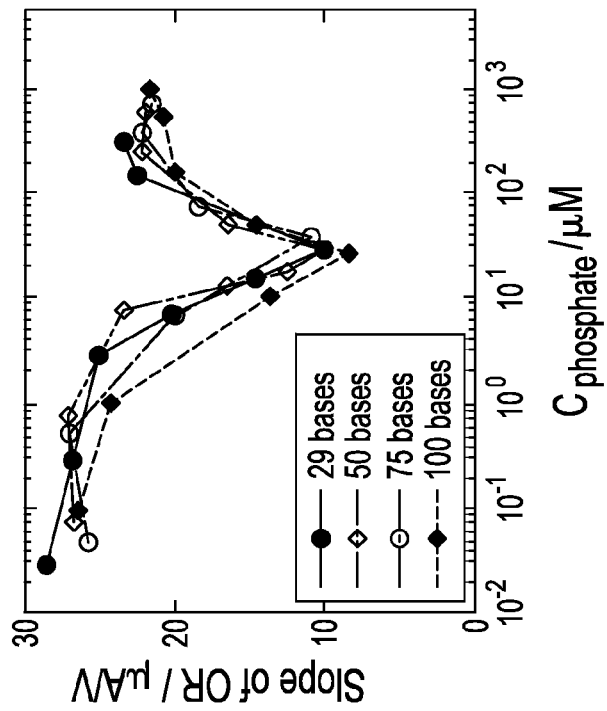
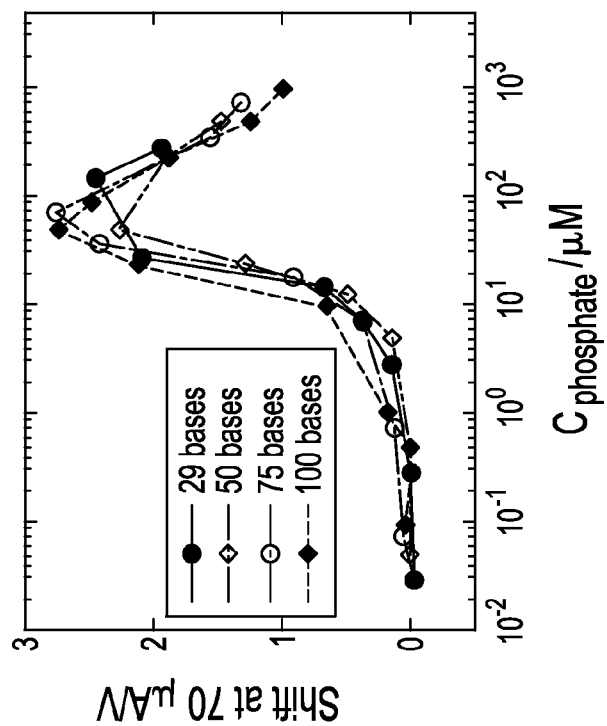
FIG. 10B

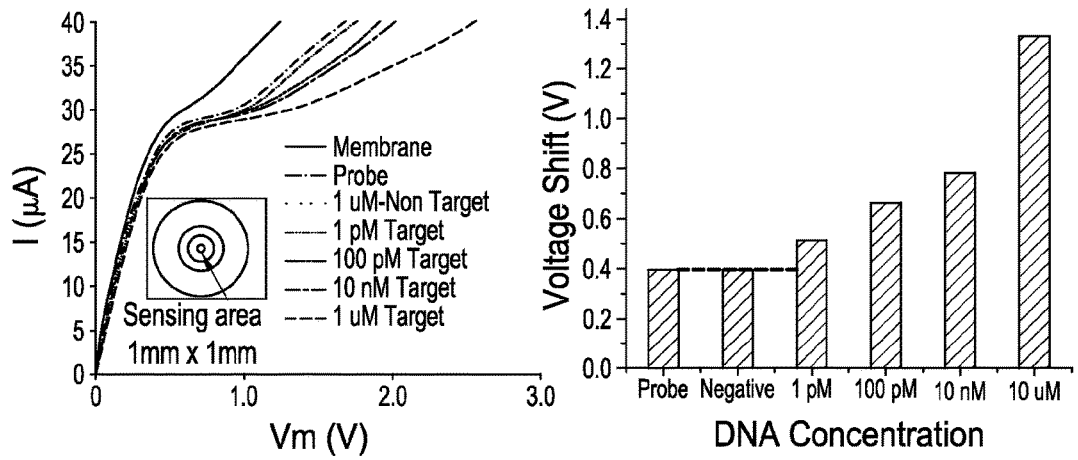
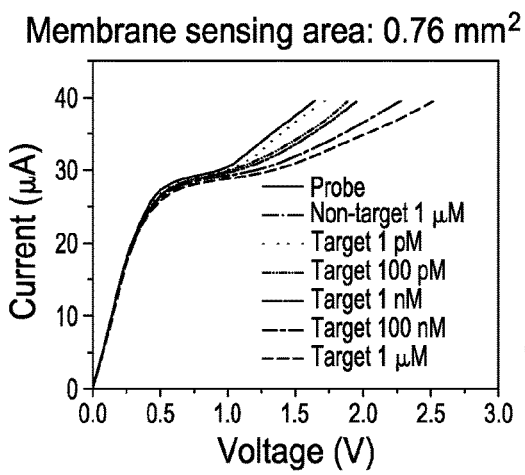
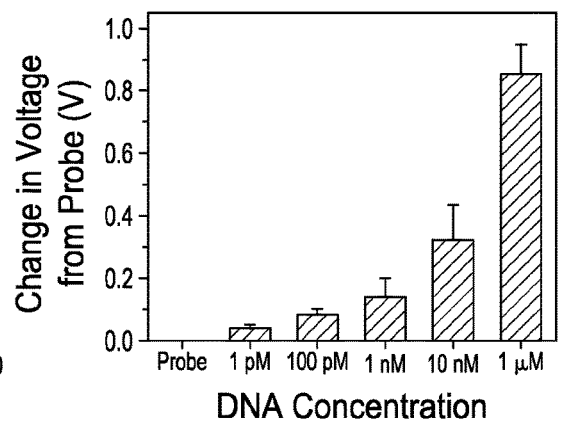
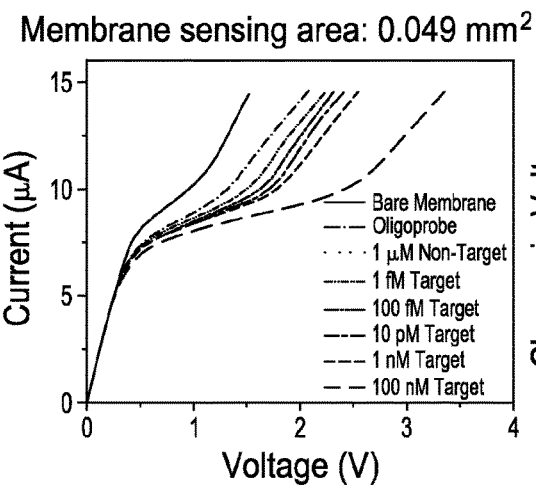
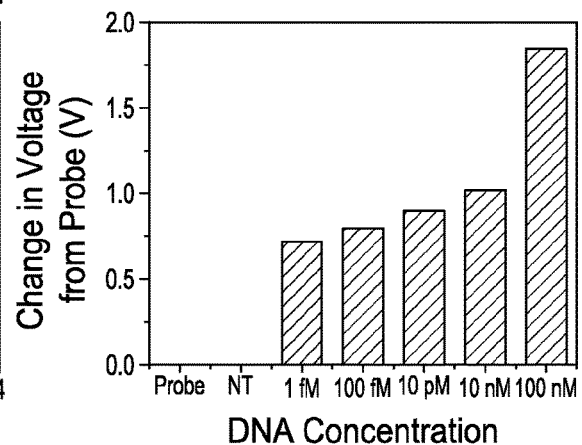
FIG. 12

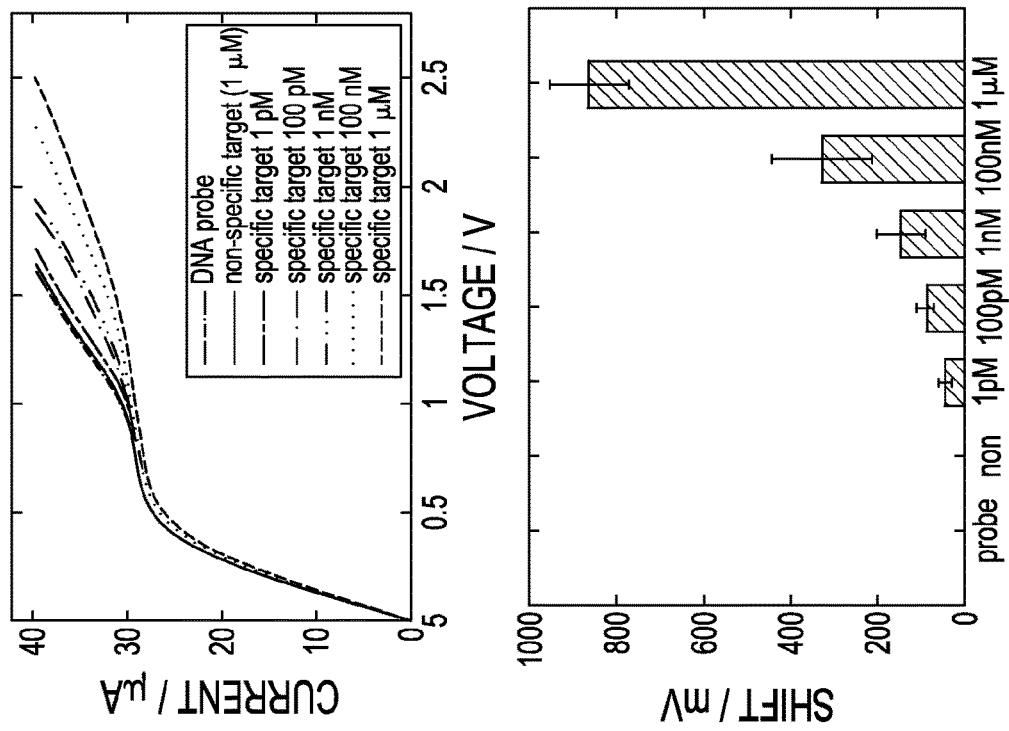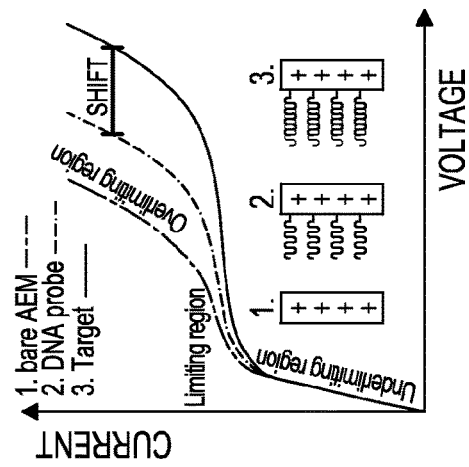
FIG. 15

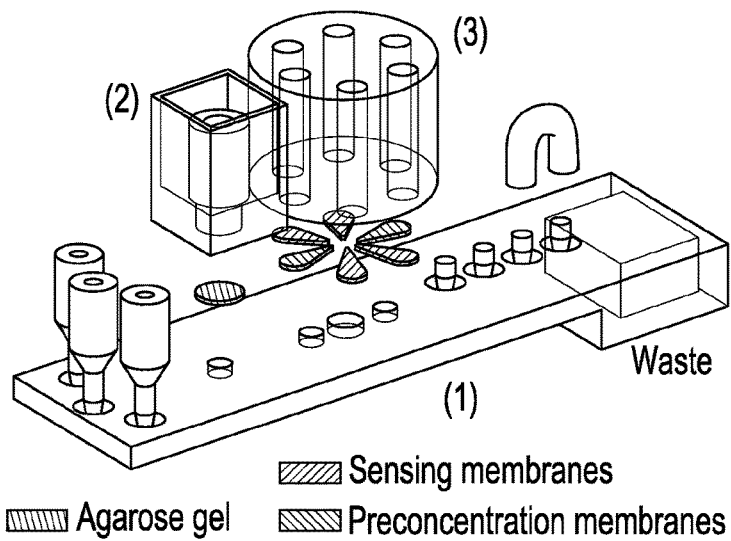
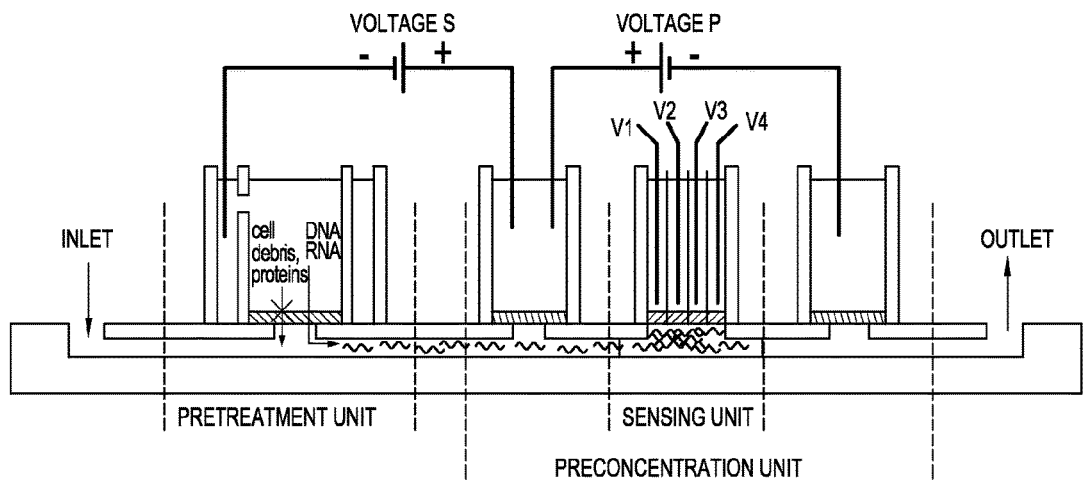
FIG. 19

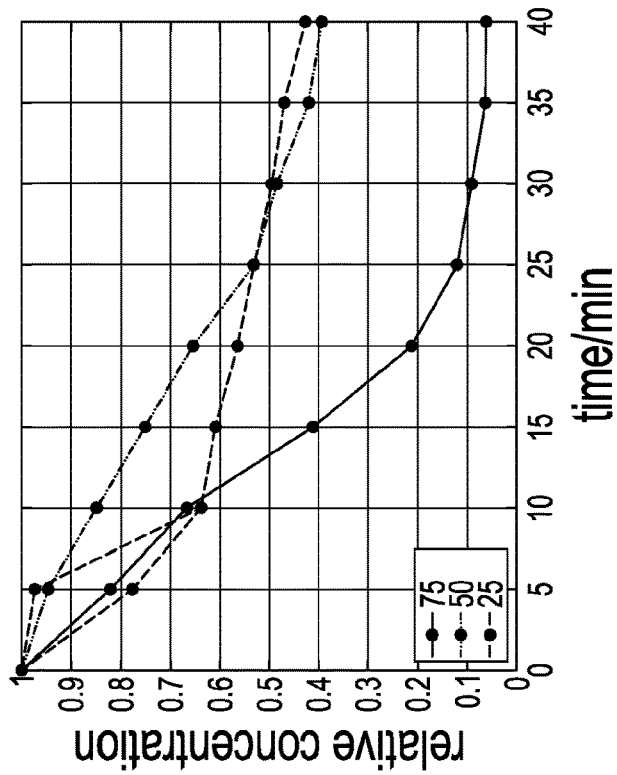
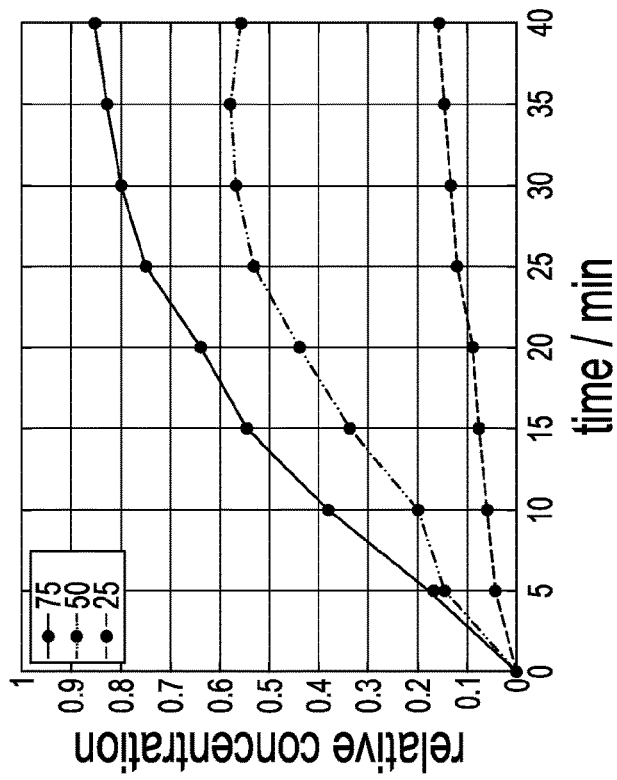
FIG. 25
(measured by UV spectrometer)

INTEGRATED MEMBRANE SENSOR FOR RAPID MOLECULAR DETECTION

CROSS-REFERENCE TO RELATED APPLICATIONS

This application is a U.S. National Phase Application of PCT International Application Number PCT/US2015/032079, filed on May 21, 2015, designating the United States of America and published in the English language, which is an International Application of and claims the benefit of U.S. Provisional Application No. 62/002,098, filed May 22, 2014, U.S. Provisional Application No. 62/051,606, filed Sep. 17, 2104, and U.S. Provisional Application No. 62/075,647, filed Nov. 5, 2014, the disclosures of which are hereby expressly incorporated by reference in their entireties.

BACKGROUND OF THE INVENTION

Field of the Invention

The disclosure relates to the field of microfluidic membrane sensing technology and more particularly, to methods and apparatus for nanomembrane based nucleic acid sensing platform.

Description of the Related Art

Dengue virus (DENV) is the world's fastest spreading tropical disease with an estimated 390 million people infected annually—three times more than the current estimate by WHO (Bhatt 2013, Mangold and Reynolds 2013). In the past several years, DENV has caused localized outbreaks in the continental U.S. (Jordan 2013). Some 3.6 billion people—about 40% of world population—are now at risk from DENV. Over two million people develop severe DENV, a serious condition requiring intensive hospital-based care, marked by internal hemorrhage (Gubler 2012, Kyle and Harris 2008). In the absence of a vaccine or any specific drug for its treatment, an early diagnosis enables appropriate supportive care that reduces disease associated morbidity and mortality (Tantawichien 2012). In addition, early diagnosis during the viremic period, which coincides with the first few days of onset of symptoms, can alert a physician to be especially watchful for warning signs of hemorrhage, which may require immediate hospital admission. Accurate diagnosis also reduces unnecessary prescription of antimalarials or antibiotics, thus reducing global drug resistance.

In the early stages of DENV infection, high levels of viremia are detected in the blood as compared to urine or saliva of the infected patient (Poloni 2010). Early diagnosis of patient's blood can thus be used as an early warning tool to identify regions of high prevalence, and institute public health measures such as insecticide spraying to control mosquitoes responsible for spreading of the disease.

While virus isolation remains the gold standard method of detecting the presence of viral pathogens, within the past couple of decades RT-PCR and ELISA-based methods have emerged as reliable diagnostic tools (Kao 2005, Lampman 2006, Lambert 2003, 2005, Pabbaraju 2009, Linssen 2000, Schmitt 2007, Saxena 2009, Weidmann 2010, Niyas 2010). However, these traditional methods of viral detection have a number of disadvantages that limit their usefulness for field applications. Results from virus isolation may take days and thus offer little actionable information during the course of an infection. ELISA techniques, although not time-consuming, typically requires 4-7 days for the body to produce appreciable antibodies by immunological response after virus infection and thus cannot be used as an early diagnostic marker. New assays are being developed which detect dengue nonstructural (NS-1) protein during acute viremia but the efficacy of these assays remains to be seen. Although the FDA recently cleared the first molecular test (CDC DENV-1-4 RT-PCR Assay) for dengue detection, the Applied Biosystems 7500 Fast Dx Real-time PCR Instrument is not portable and thus precious time is spent transporting specimens (2-3 hours of test time+potentially 24-48 hours of sample delivery time) and waiting for the results to return. A 2-3 hour result is a significant improvement but the complexity of such systems including its lack of portability, expensive reagents and requirement of technical personnel for operation become an economic disadvantage.

According to the FDA, two main groups of nucleic acid based diagnostic tests have been approved. The first group is for human genes and the other group is microbial tests. There are over 30 tests for human genetic detection, including, for example, cystic fibrosis, breast cancer, and prostate cancer. There are over 100 tests for microbial testing, including, for example, testing for E. coli, hepatitis, and enterococcus. In general, the tests use one of two specific detection assays. The first assay is called FISH (fluorescent in situ hybridization). The second assay consists of a few steps including some treatments of the sample, which usually means separation of nucleic acids from real samples (or raw samples), followed by PCR amplification, and subsequent optical detection, such as fluorescence detection. Each of these steps usually involves highly skilled investigators. Often a medical doctor is required to analyze and interpret the test results.

While there is abundant literature on DNA sensing technologies, little is reported about RNA detection. Among the RNA sensing technologies, most of the technologies rely on fluorescence-labeling for optical detection such as molecular beacon (Marti 2007), Förster resonance energy transfer (Sando and Kool 2002, Socher 2008) and dye-trapping liposomes (Baeumner 2004). Some optical detection techniques, for instance surface plasmon resonance imaging (SPRi) microarray (Nelson 2002) and mass-sensitive detection such as microcantilever designs (Zhang 2006) are label free, but require expensive equipment and have signal instability issues. Although these optical detection methods provide reasonable detection limits down to an impressive single molecule level, they all require costly, bulky optical systems.

Several label-free molecular sensing technologies like electrochemical sensors that amplify signal using redox reporters enhance detection sensitivity, yet are hampered by instability of the electrochemical signal and difficulty in calibration (Bakker and Qin 2006, Umezawa and Aoki 2004). Capacitance, conductance and field effect transistor (FET) electrode sensors are typically insensitive as the ionic strength within the electrical Debye layer on the electrode is about 2 to 3 times higher than the bulk and the presence of the RNA molecules would not significantly affect the local conductance (Stern 2007, Suni 2008). They are also expensive since they require fabrication of microelectrodes. Most importantly, the largest drawback of all electrode sensors is their long assay time due to diffusion-based transport of large target molecules like DNA/RNA to the electrode surface (Nkodo 2001). Several techniques have been suggested to remove the slow transport of large nucleic acid molecules to the electrode sensor. One involves the activation of high voltage at the electrode sensor to electrophoretically attract nearby DNAs (Sosnowski 1997). However, this electrophoretic concentration technique is highly nonspecific and the elevated voltage can produce undesirable Faradaic reactions for high ionic strength buffers resulting in false current or voltage signals.

Therefore, the major disadvantages of existing detection technologies are 1) time consuming, 2) expensive, 3) require trained personnel and 4) not suitable for field diagnostics. Thus, the lack of availability of a point-of-care diagnostic platform has made the detection of viruses in human sera particularly cumbersome in endemic areas.

SUMMARY OF THE INVENTION

The devices and methods of the disclosure each have several aspects, no single one of which is solely responsible for its desirable attributes. Without limiting the scope of this disclosure as expressed by the claims which follow, its more prominent features will now be discussed briefly. After considering the following detailed descriptions and drawings, one will understand how the features of this disclosure provide advantages that include an integrated membrane sensor for the rapid detection of molecular species, as described herein.

A membrane sensor was developed as a means of detection for DNA, RNA, etc. and is documented in *A Nanomembrane-Based Nucleic Acid Sensing Platform for Portable Diagnostics* (Senapati, et al, 2011) and in U.S. patent application Ser. No. 13/476,783, filed May 21, 2012.

The article *Microfluidic Systems with Ion-Selective Membranes* (Slouka, et al, 2014) provides background on the integration of several systems into a single system for the processing of real samples for the detection of molecules.

In some embodiments disclosed herein is a microfluidic sensing device and method wherein the device is a nucleic acid sensing platform capable of rapid, high throughput, accurate, and reliable identification of pathogen-specific nucleic acids in a field-expedient format. Molecular detection is accomplished without amplification of nucleic acid, using an extremely sensitive nanomembrane-based electrokinetic sensor, capable of detecting DNA or RNA target sequences. Without the need for thermocycling or a dedicated heat block, the detection platform described herein is rapid, sensitive, low-cost, easy to use, and portable, making it amenable to point-of-care applications. The device described herein is therefore capable of evaluating human clinical specimens for the presence of pathogen-specific RNA and thus provide critical information during a rapid response to an emerging infectious disease outbreak or a bioterrorism event. Development of a cost-effective, point-of-care diagnostic instrument for rapid, sensitive and specific detection of DENV from patients can help to circumvent many inherent difficulties related to control of dengue fever and severe dengue.

In some embodiments disclosed herein, the microfluidic sensing device is used for the detection of viral nucleic acids. One of skill in the art would readily recognize that viral nucleic acids could be selected from any particular virus, and could include, as an example, dengue virus (DENV). DENV is a model organism, and examples are used throughout the disclosure to demonstrate the capability of the microfluidics device, but it should be understood that the embodiments disclosed herein are not intended to be limited to DENV. In addition, one of skill in the art would recognize that the methods and devices disclosed herein are applicable to the detection and quantitation of various target molecules, including biomolecules. Most biomolecules are charged, and nucleic acids stand out in particular because they bear a strong negative charge.

DENV is an RNA virus with four different serotypes (DENV-1, 2, 3, 4). While the RNA of the virus is stable within the viral shell, the chances of RNA degradation increase during the extraction phase if exposed to ubiquitous RNase enzymes. RNA detection therefore represents a higher bar than DNA, which the platform can overcome. DENV is also a National Institute of Allergy and Infectious Disease (NIAID) Category A pathogen, and a rapidly emerging global public health threat. Early diagnosis of dengue therefore has significant clinical importance, and can help facilitate appropriate supportive therapies to reduce DENV associated morbidity and mortality. In austere environments where RNA preservation cannot be easily carried out, an integrated diagnostic assay capable of RNA extraction and detection with minimum human intervention represents an urgent global health need.

In one embodiment disclosed herein, the integrated platform comprises: an upstream pre-treatment unit capable of capturing RNA from DENV samples including human clinical samples; a nanomembrane-based RNA pre-concentration unit to concentrate the extracted nucleic acids; and a multiplexed RNA biosensing unit capable of detection and identifying any of the four DENV serotypes. As should be understood by those of skill in the art, the detection technology is adaptable and can be used for nucleic acid-based detection of other pathogens of interest from a variety of sample matrices, including human clinical and environmental samples.

The integrated chip disclosed herein utilizes a unique fabrication process that is developed to integrate different functional units solely based on the behavior of heterogeneous ion-exchange membranes in DC field into a single microfluidic chip for sample-to-answer automated detection of target pathogen by identifying nucleic acid or protein biomarkers. The intended use of the integrated chip is for fast and in-field (point-of-care) screening or diagnosis of cancer and pathogen-caused diseases from chemically or electrically lysed samples. The units integrated on the chip are pre-treatment unit, pre-concentration unit, and sensing unit connected to a common main channel. One of skill in the art would recognize that the DC (or sometimes also AC) electrical field can be used to manipulate the charge on the molecules thereby moving the whole molecule.

The pre-treatment unit for a real or raw sample (for example, blood, saliva, water, or urine) lyses the cells, bacteria, viruses, and other bioparticles to release the biomarkers. Upon application of a DC field, the negatively charged biomolecules are pulled out of the lysate through a thin layer of agarose gel towards the positively biased electrode. The agarose gel serves as a mechanical barrier between the sample chamber and the main channel on the chip. Nanoporous heterogeneous cation exchange membranes contain negative fixed charge that does not allow the passage of negatively charged molecules (nucleic acids/proteins) due to both steric effect and strong electrostatic repulsion. The pretreatment unit thus allows selective separation of negatively charged biomolecules from the lysate and their containment in another fluidic chamber for further downstream processing.

The pre-concentration unit is composed of two cation exchange membranes that when under DC bias, generate a non-homogeneous electrical field profile (depletion region) in the main channel. The combination of this electric field profile and the opposite pressure driven flow in the main channel can be used to concentrate the previously extracted biomolecules precisely in one location. The pressure driven flow (constant along the channel) and the electromigration of negatively charged biomolecules (changes along the channel) act on the biomolecules in opposite directions and the molecules localize at a position where these two effects cancel each other out. This localized position of the target biomolecules is where our sensing unit for the integrated platform will be placed.

Any kind of heterogeneous anion exchange membranes/optical/plasmonic/electrochemical sensor capable of detecting target biomarkers (nucleic acids, proteins, etc.) is inserted in the sensing unit slot for detection. The sensing unit can contain an array of sensors each targeting different RNA or DNA or protein molecules for the detection of multi-target analytes.

Different designs of the three aforementioned units and the fluidic structures are first fabricated as stand-alone units and then put together using adhesives. The fluidic structures are made in plastic sheets that are assembled by thermal fusing. The three units are made through a combination of molding processes for precise membrane positioning and various auxiliary techniques (micromachining, drilling, etc.) for the whole unit assembly. All the techniques are inexpensive and easy to use without requiring highly trained personnel. The platform is novel in that it not only extracts, concentrates and detects on-chip, but is also capable and amenable to change/switch out all the three components including a variety of potential biosensors.

In some embodiments, the integrated platform can be used for detection of dengue virus, brucella, *E. coli*, and micro RNA markers associated with oral cancer. However, the potential technological capability and application is much broader and can be used for other medical diagnostic applications, water, and environmental safety and for some food safety markets given that the target sample has/is capable of being converted into fluid properties.

The integrated nucleic acid detection platform circumvents the issues associated with electrochemical/fluorescent-based sensing techniques by reducing assay cost, assay time, improving sensitivity, stability and portability for point-of-care applications. As described herein, and as will be readily apparent from the following descriptions of the drawing and exemplary embodiments, the platform enables molecular detection in a miniature format, amenable to use in any setting where such detection is required—be it near the patients' bedside at a sophisticated hospital, or in a clinic in a low resource setting, or by first responders investigating a biological event or a medic at a military base.

In one embodiment, a system is disclosed for detecting target biomolecules in a sample, the system includes a control unit and an integrated chip. The control unit includes a pumping system comprising at least one pump fluidly coupled to a fluidics system comprising at least one fluidic channel, wherein the at least one pump is configured to generate fluid pressure and flow within the fluidics system. The control unit also includes a voltage-current source, an analysis-output module, and a programmable controller, operably coupled to and configured to control the pumping system, the voltage-current source, and the analysis-output module. The integrated chip is configured to insert reversibly into the control unit, and fluidly coupled to the pumping system, electrically coupled to the voltage-current source, and operably coupled to the analysis-output module. The integrated chip includes:

a pre-treatment unit, comprising a fluid inlet in fluid communication with the pumping system, and a sample inlet, wherein the pre-treatment unit comprises a pre-treatment fluidic channel, at least two electrodes coupled to the voltage-current source and configured to generate an electric field within the pre-treatment fluidic channel, and a molecular filter within the pre-treatment fluidic channel, such that sample molecules flowing through the pre-treatment fluidic channel are separated by both charge and by molecular weight;

a pre-concentration unit, comprising at least two ion exchange membranes disposed along a pre-concentration fluidic channel, and at least two electrodes coupled to the voltage-current source and configured to generate an electric field within the pre-concentration fluidic channel, wherein the pre-concentration fluidic channel is fluidly coupled to the pre-treatment fluidic channel and the pumping system, such that sample molecules are concentrated within the pre-concentration fluidic channel at a location where opposing flow and electrophoretic forces are substantially equivalent; and a sensor unit comprising an ion exchange membrane disposed between first and second fluidic channels, wherein one of the fluidic channels is fluidly coupled to the pre-concentration fluidic channel and the pumping system, wherein the ion exchange membrane is functionalized with a probe complementary to the target biomolecule, and a first pair of opposing electrodes positioned within the first and second fluidic channels on opposite sides of the ion exchange membrane, wherein the first pair of opposing electrodes are configured to apply an input signal across the ion exchange membrane, and a second pair of opposing electrodes positioned within the first and second fluidic channels on opposite sides of the ion exchange membrane, wherein the second pair of opposing electrodes are configured to measure an output signal.

In one variation to the system, the fluidic system further comprises at least one fluid reservoir and at least one waste reservoir.

In another variation, the at least one pump comprises an electroosmotic pump, a valve and syringe system, or both an electroosmotic pump and a valve and syringe system.

In another variation, the molecular filler in the pre-treatment unit comprises a nanofilter, a hydrogel, or a nanofilter and a hydrogel.

In another variation, the pre-treatment unit further comprises a cation exchange membrane disposed along the pre-treatment fluidic channel.

A method for quantifying the presence of a target biomolecule in a sample is disclosed in accordance with another embodiment. The method includes:

introducing the sample to an integrated membrane sensor via a sample inlet;

flowing the sample through a pre-treatment fluidic channel comprising a molecular filter and at least two electrodes coupled to a voltage-current source and configured to generate an electric field within the pre-treatment fluidic channel, wherein target biomolecules in the sample are separated from other biomolecules by both charge and by molecular weight;

flowing the separated target biomolecules through a pre-concentration fluidic channel, comprising at least two cation exchange membranes disposed along the pre-concentration fluidic channel, and at least two electrodes coupled to a voltage-current source and configured to generate an electric field within the pre-concentration fluidic channel, wherein target biomolecules are concentrated within the pre-concentration fluidic channel at a location where opposing flow and electrophoretic forces are substantially equivalent;

flowing the concentrated target biomolecules through one of a pair of fluidic channels separated from one another by an ion exchange nanomembrane, wherein the nanomembrane is functionalized with a probe configured to bind the target biomolecule, and wherein the nanomembrane and the target biomolecule are oppositely charged;

applying limiting and overlimiting current across the nanomembrane; and detecting a change in electrical potential across the nanomembrane, wherein the change in electrical potential is related to the target biomolecule binding to the probe, thereby quantifying the presence of the target biomolecule.

In on variation to the disclosed method, an AC sinusoidal electromagnetic perturbation is provided while detecting the change in electrical potential across the nanomembrane. In other variations, chemical and reagent processes aid in the preparation of the sample to analyze proteins, genes, or other target molecules. Many processes exist to amplify gene expression, DNA, proteins, or other targets in PCR or other lab processes. This chemical "preparation" for hybridization would allow for detection with the disclosed sensor. In other examples, positive molecules can also be detected.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments, and are not intended to be limiting in scope.

FIG. 10B shows the shift in voltage and slope of OR as a function of concentration of phosphate groups forming sugar-phosphate backbone of nucleic acids for ssDNA of different lengths.

FIG. 12 depicts the change in the CVC shift for various concentrations using a membrane having various sizes.

FIG. 15 shows the results of the nanomembrane based nucleic acid sensing platform. The graph on the left depicts the shift in the current voltage curve that occurs for bare anion exchange membrane, anion exchange membrane with a DNA probe attached thereto, and the membrane with target. The graphs on the right depict current voltage curves for various concentrations of target, emphasizing the ability to quantitate the target based on the shift in the curve.

FIG. 19 depicts one embodiment of the integrated chip wherein the sensor comprises several integrated chips each with their own targets.

FIG. 25 shows the measurement of the electrophoretic extraction of ssDNA from the sample reservoir into the loading reservoir of the pretreatment unit. The ssDNA concentration was measured on a UV-Vis spectrometer (NanoDrop 2000). As the concentration of sample in the sample reservoir decreased, the concentration in the loading reservoir increased.

DETAILED DESCRIPTION OF THE PREFERRED EMBODIMENTS

Figure 1A:
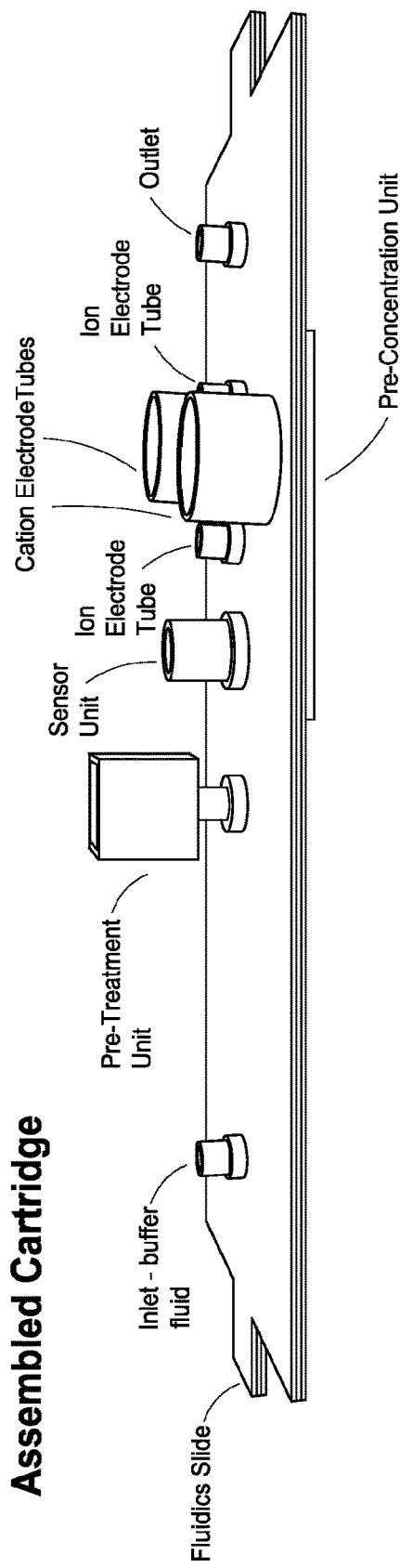
FIG. 1A depicts one embodiment of an assembled microfluidic membrane sensing apparatus as disclosed herein.

Although the invention is described in various exemplary embodiments and implementations as provided herein, it should be understood that the various features, aspects, and functionality described in one or more of the individual embodiments are not limited in their applicability to the particular embodiment with which they are described. Instead, they can be applied alone or in various combinations to one or more of the other embodiments of the invention, whether the embodiments are described or whether the features are presented as being a part of the described embodiment. The breadth and scope of the present invention should not be limited by any exemplary embodiments described or shown herein.

The disclosure relates generally to methods and apparatus that complement the traditional techniques of biomolecular tools for nucleic acid assays. In some embodiments of the disclosure provided herein are microfluidic-based platforms that are compatible with point-of-care diagnostics and/or screening.

The nanomembrane based nucleic acid sensing platform for portable diagnostics as described herein provides significant advantages, benefits, and novel features for the detection of nucleic acids. These advantages include, for example: low-cost manufactured devices using simple chip fabrication; signal stability, as the sensor measures ion-current and the sensing signal is stable due to absence of noise-sensitive electron-transfer reactions, the signal is robust and target specific; sensitivity and selectivity by means of a sensor that is capable of distinguishing single base pair mismatch in the target sequence and quantifying nucleic acids concentration comparable to or better than the current gold standard; multiplexing capabilities provided wherein the platform is capable of detecting more than one nucleic acid sequences, such as, for example, DENV-1, 2, 3, and 4; simplicity of assay protocol based on the simple design and portability of the device, which eliminates the need for any lab facility or trained personnel, such that the integrated platform is a push-button, automated sample-to-answer device; decreased assay time because the use of a target pre-concentration technique, which reduces diffusion time, allows for rapid sensing and enhanced sensitivity and sample preparation to detection is complete in a matter of minutes; and adaptability, such that the platform technology is readily extended to the detection of any pathogen of interest.

Terminology

Control Unit—This is sometimes referred to as the platform or a platform or complete System.

Integrated Chip—The term chip is also referred to as chip, lab-on-a-chip or microfluidics chip.

Pre-Treatment Unit—This is also referred to as the Molecular Separation Unit, MSU.

Pre-Concentration Unit—This is also referred to as the Molecular Concentration and Localization Unit or MCLU.

Sensor Unit—Detection Unit and membrane sensor are sometimes used to describe the Sensor Unit.

Reservoir & Fluids Channel—Reservoir or chamber that holds fluids and is sometimes used, especially in early embodiments, in place of channel or fluidics channel. Reservoir in later embodiments is separate from channel. Though both the fluids channel and reservoirs house fluids throughout the embodiments.

As will readily become apparent by reference to the figures and disclosure, the devices and methods disclosed herein have numerous applications, such as, for example: detection of nucleic acids of varying lengths of nucleotides from biological samples that include humans, animals, plants, etc.; infectious disease detection, diagnosis; replace sensing technologies of PCR including visual detection through fluorescence; standalone system for many situations and environments from individual use to high throughput systems to in office/desktop systems for researchers, healthcare practitioners, inspectors, etc.; water safety; environmental testing and purification involving liquids; genetic testing for specific genes and sequences; double or single stranded nucleotide detection and identification; isolation of molecules based on charge (positive or negative); concentration of molecules based on charge (positive or negative); sorting of molecules by species; filtration of molecules by size, molecular mobility in electrical field, and charge; separation of molecules by size, molecular mobility in electrical field, and charge; manipulation, placement, and movement of molecules in a liquid; used in a series of pretreatment units and pre-concentration units to refine, sort, filter, separate contents in a liquid; national security and defense in detection, prevention, research, etc. of disease, invasive species of plants and animals biohazards, etc.; microbial detection; liquid purification, manufacture of de-ionized water, sorting of molecules; positive charge molecular separation; negative charge molecular separation; move molecules to predetermined locations in a fluidics channel to sense, concentrate, or other uses; diagnostic, screening, therapeutic determination, prognosis, companion diagnostics; used in the research and development of all applications listed; removal of dyes, pollutants, or targeted molecules from liquids; quantification of target molecules; and control movement of molecules within fluids for delivery or removal of targeted molecules.

Figure 1B:
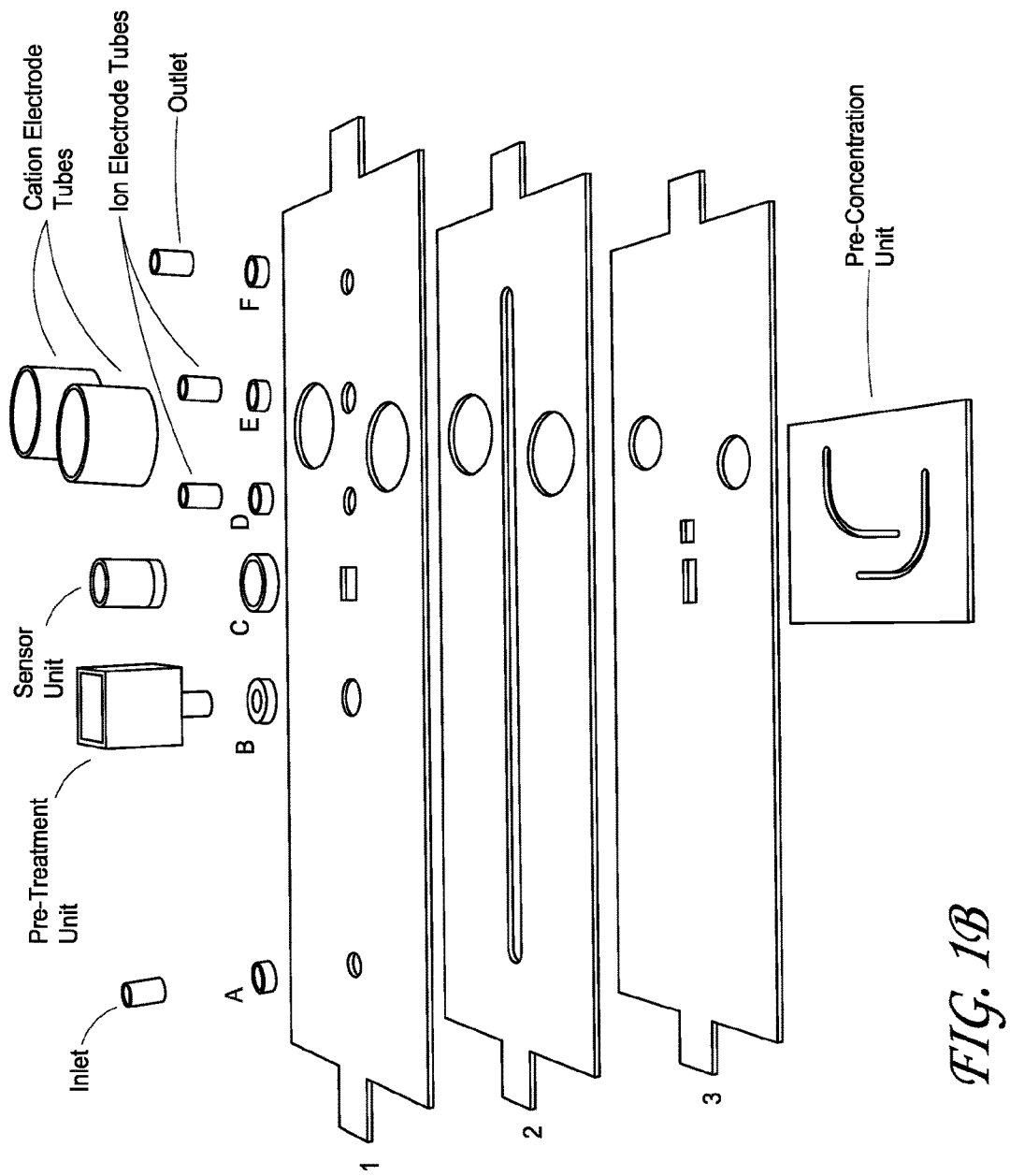
FIG. 1B depicts an exploded view of the embodiment of the apparatus as described in FIG. 1A.

The following disclosure is structured to detail each separate unit of the integrated membrane sensor, including a disclosure of the integrated chip and the control unit. The fully integrated chip is illustrated in FIG. 1A, with an exploded view in FIG. 1B. As shown in FIG. 1, the integrated chip includes a sensor unit, a pre-concentration unit, a pre-treatment unit, and several additional periphery components to provide structure and housing to the integrated chip. A sensor unit is a unit of the invention that is used as a means of detecting and quantifying molecules. However, additional units are required to improve the sensitivity and specificity of the sensor unit, including the pre-concentration unit, the pre-treatment unit, and the pump system. Each unit can be used as a module in other systems, as further described herein.

Figure 2:
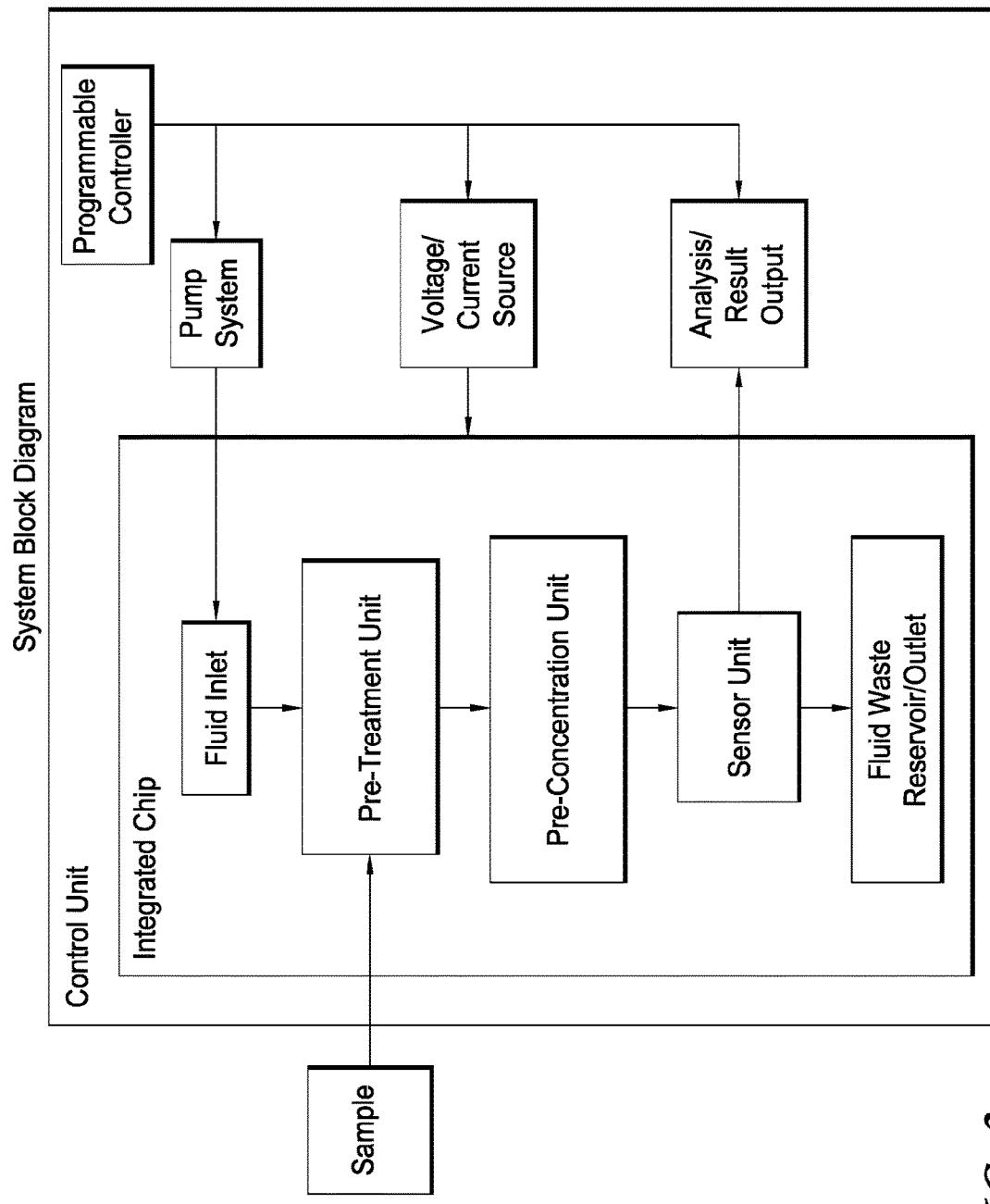
FIG. 2 depicts one embodiment of a system block diagram as described herein, wherein the system block diagram comprises various units and components. In one embodiment, the Control Unit may house an integrated chip, a pump system, a voltage/current source, an analysis/results output, and a programmable controller.

As shown schematically in FIG. 2, one embodiment of a microfluidics chip as disclosed herein integrates several units to analyze biological samples. The units include a pre-treatment unit, pre-concentration unit, sensor unit, pumping system, and peripheral components. Each component has specific capabilities and the ability to function when not integrated into the chip. The fully integrated chip is capable of separating, filtering, transporting, localizing, concentrating, detecting, and quantifying molecules. In the embodiment shown in FIG. 2, a control unit houses the pump system, voltage/current source, analysis/results output, and the programmable controller. These automate the functions of the integrated chip. The sample is inserted into the integrated chip. The sensor unit is capable of detecting and quantifying molecules. One of skill in the art would readily recognize that there are several designs of each unit, and that the components of the chip need not necessary be designed as shown in the embodiment of FIG. 2.

Sensor Unit

The sensor unit is capable of detecting and quantifying molecules. The sensor unit is capable of being a standalone unit, but can also be used as part of the integrated chip, which improves the sensitivity and the specificity of the sensor unit. The sensor unit measures specific and targeted molecules that hybridize on a probe. The molecules are transported and localized near the probes through pipette, or through other units in the integrated chip including the pre-treatment unit and pre-concentration unit. The targeted molecules hybridize on the probes. After a period of hybridization is allowed, the probes are washed to remove non-specific molecules or the non-targeted molecules. Finally, the specifically targeted molecules are detected and quantified.

Because nucleic acids are negatively charged, a positively charged membrane can be used to detect nucleic acids. The structure of nucleic acids is a repetition of four main nucleotides which are connected through a sugar phosphate backbone. From the point of electrical chemistry or electrokinetics, this sugar phosphate backbone is negatively charged. The charge sitting on these nucleic acids is very important. It can be used as a handle for those molecules to manipulate them, transport them, or to pre-concentrate them. But at the same time, this charge can be thought of as an intrinsic tag that is used to detect those molecules.

Ion exchange membranes, such as anion exchange membranes having a positive fixed charge, including, for example R—$(CH_3)_3N^+$ or cation exchange membranes having a negative fixed charge, including, for example R—$SO_3^-$, are used in various electro-membrane-separation industries as effective means to enhance or suppress the transport of ions. Traditional uses of ion exchange membranes are for water treatment, electrodialysis, and electrodeionization. These ion exchange membranes can be homogeneous or heterogeneous. The heterogeneous ion exchange membranes contain finely ground ion exchange particles possessing high concentration of functional groups responsible for the formation of fixed charge evenly dispersed in polyethylene or polypropylene which serves as a binder. These membranes are reinforced typically with polyester or polyimide fibers. The major functioning component is the ion exchange particles.

Ion exchange membranes exhibit a property of ion selectivity that is given by: (i) they contain high concentration of a fixed charge and (ii) their internal structures have characteristic dimensions on the nanometer scale. Ion selectivity and the behavior stemming from ion selectivity and applied DC electrical field is used to separate, concentrate, and detect targeted molecules.

In one embodiment, a first ion exchange membrane is an anion exchange membrane and is functionalized with quaternary ammonium groups that provide a positive charge. A second ion exchange membrane is a cation exchange membrane, which is functionalized with sulfone groups that provide a negative charge. These charges make the ion exchange membranes ion selective. Mobile counter-ions (ions with opposite charge to that one of the fixed charge) penetrate through the membrane.

One of the advantages of the membranes disclosed herein is that small-enough counter-ions can travel through these membranes. Small is defined as a molecular weight of less than approximately 300 g/mol. The ability of counter ions to penetrate these membranes increases with decreasing molecular size. Ions larger than the defined ranges of the particular membrane embodiment are absorbed onto the membrane.

Figure 3:
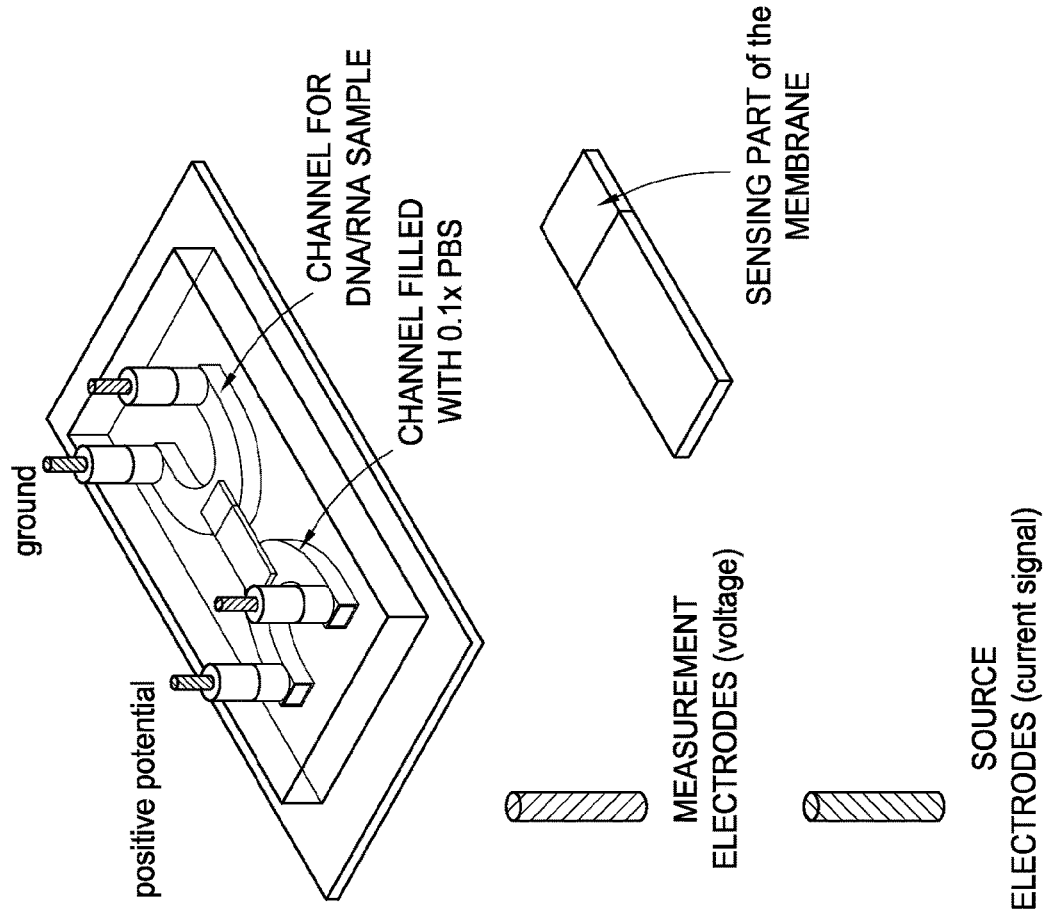
FIG. 3 illustrates one embodiment of the nanomembrane based nucleic acid sensing platform for portable diagnostics having two channels bridged by a membrane atop the channels. The platform additionally comprises source electrodes and measurement electrodes

FIG. 3 depicts one embodiment of a sensor unit. The unit has two channels bridge by an ion membrane on top of the channels. DNA solution is placed in one of the channels and the DNA was allowed to absorb onto the membrane. A current voltage curve (CVC) was measured. As shown in one embodiment of FIG. 3, the two channels are housed in a polymeric slab made of poly-dimethyl siloxane. The membrane connects the two channels. Each of the channels is filled with 0.1×PBS and one of the channels also contains a sample which includes target molecules, for example nucleic acids. However, the solutions contained in the two separate channels do not mix with convection. They are only connected through the membrane, which can carry the electricity via the movement of ions. The channels can be closed and the membrane sensor connects the current flow path between the channels.

Because the charge of the membrane is positive and the target nucleic acid molecules are negative, there is a very strong electrostatic attraction between the membrane and the molecules, and thus, the nucleic acid molecules from the immediate vicinity of the membrane are drawn to the membrane and absorb on its surface. The nucleic acids cannot enter the membrane, but they can absorb on the surface. The channels are filled with an electrolyte, such as KCl. One measurement electrode is placed in each channel and a current source electrode is also placed in each channel.

Figure 4:
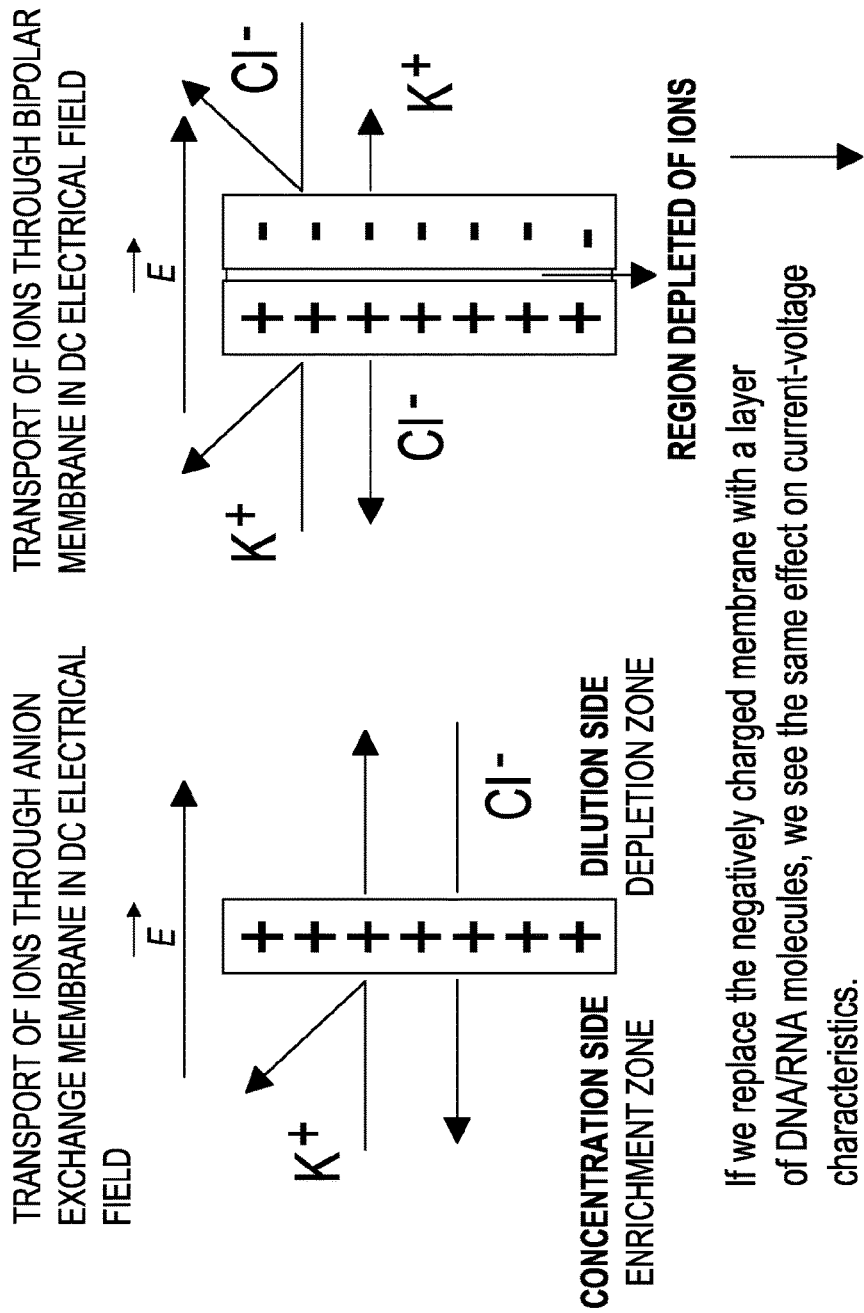
FIG. 4 illustrates a detailed view of the interaction that takes place on the surface of the membrane, wherein one embodiment of the apparatus includes a positively charged membrane, and another embodiment includes a bipolar membrane (both a positive and a negative membrane together).

FIG. 4 depicts the interactions of molecules on the surface of a membrane. Because the nucleic acid is negatively charged and the membrane is positively charged, the nucleic acid is drawn towards the membrane until it absorbs on the surface. When a DC current is applied with one side of the membrane negative and the other positive, then the anions can go through the membrane. This happens because the opposite charges on each side of the membrane cause the anions to attract to the positive side of the membrane.

Unlike anions, cations are attracted towards the membrane because they are positively charged and are attracted toward the negative side of the membrane. However, there will be many cations along the membrane and this will cause an electrostatic repulsion. As a result, the cations are unable to move through the membrane and they remain on the side of the membrane with the positive charge.

Consequently, the anions are removed from one side of the membrane while the cations are prevented from leaving the positive side of the membrane. This leads to a concentration of ions on one side of the membrane. At time zero, the concentration is the same everywhere in both channels of ions. When the voltage is applied, there is a flux of ions and the concentration of ions on one side goes up and the concentration of ions on the other side goes down.

When negatively charged molecules are fixed on the surface, such that negative molecules are sitting on the positively charged membrane, the anions that would normally go through the membrane will feel some repulsion. As a result, there is a measurable change that is detected with a current voltage curve. In essence, the nucleic acid that is in the channel is drawn towards the membrane because the membrane is positively charged and the nucleic acid is negatively charged. The nucleic acid is absorbed onto the surface of the membrane facilitated by the electrostatic interaction.

As shown in FIG. 4, in one embodiment of the membrane, an ion exchange membrane is connected to a DC electrical field. The contra-ions or in this case anions can easily penetrate through the membrane. Cations, however, do not go through the membrane.

Figure 5:
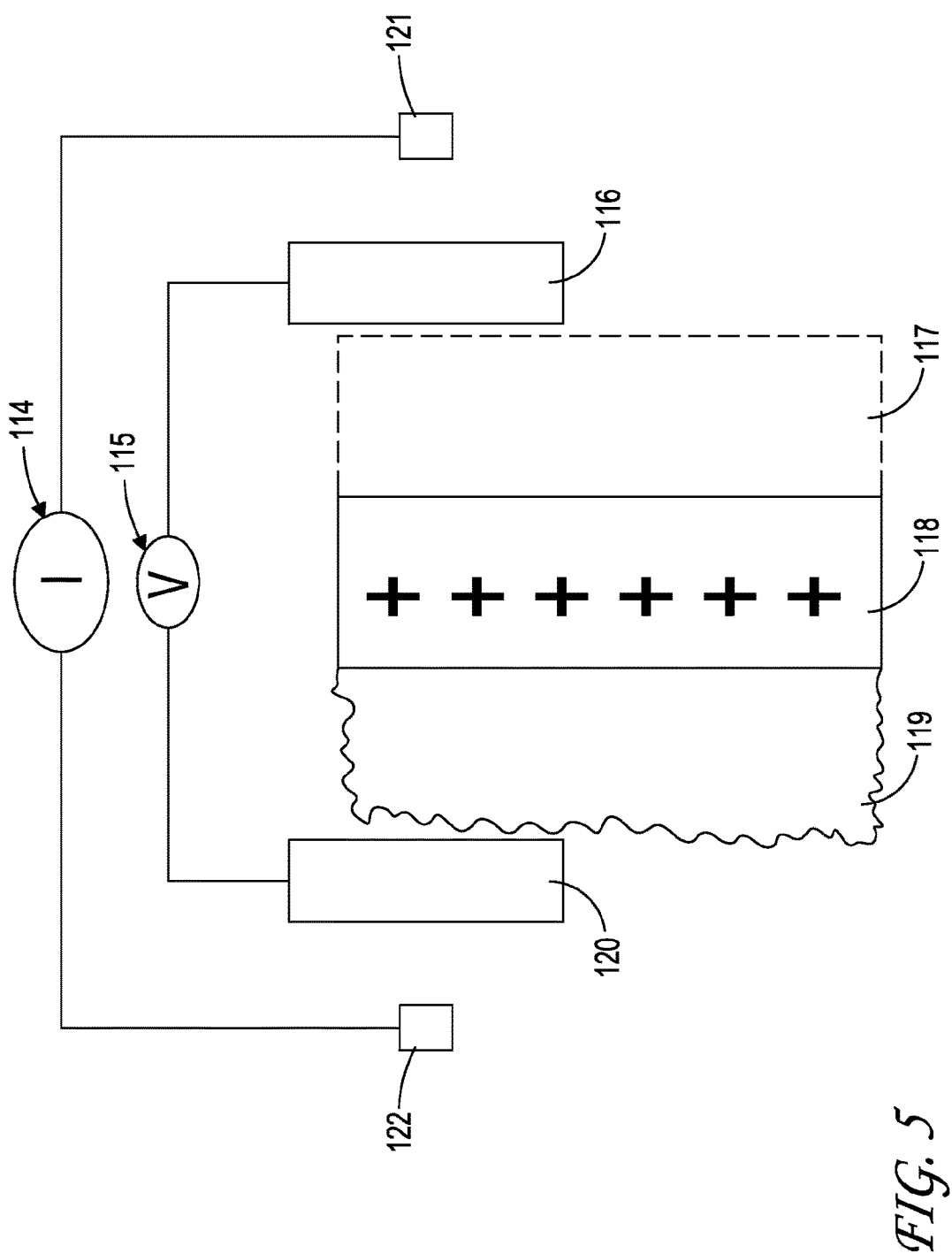
FIG. 5 diagrams one embodiment of the methods of the invention, wherein a pair of electrodes is placed within the microfluidic channels of the sensing platform. In one embodiment, current is applied and voltage is measured across the membrane.

FIG. 5 depicts one embodiment of the invention, wherein a diagram depicts the application of current across a membrane. The current is applied through the current diagram and measured through the voltage diagram. Four electrodes are used, with two on each side of the membrane. The voltage is measured on the side with the DNA. Two of the electrodes measure the voltage across the membrane plus some adjacent electrolyte. The other pair of electrodes connects a current signal to the membrane, which is applied and measured.

Figure 6:
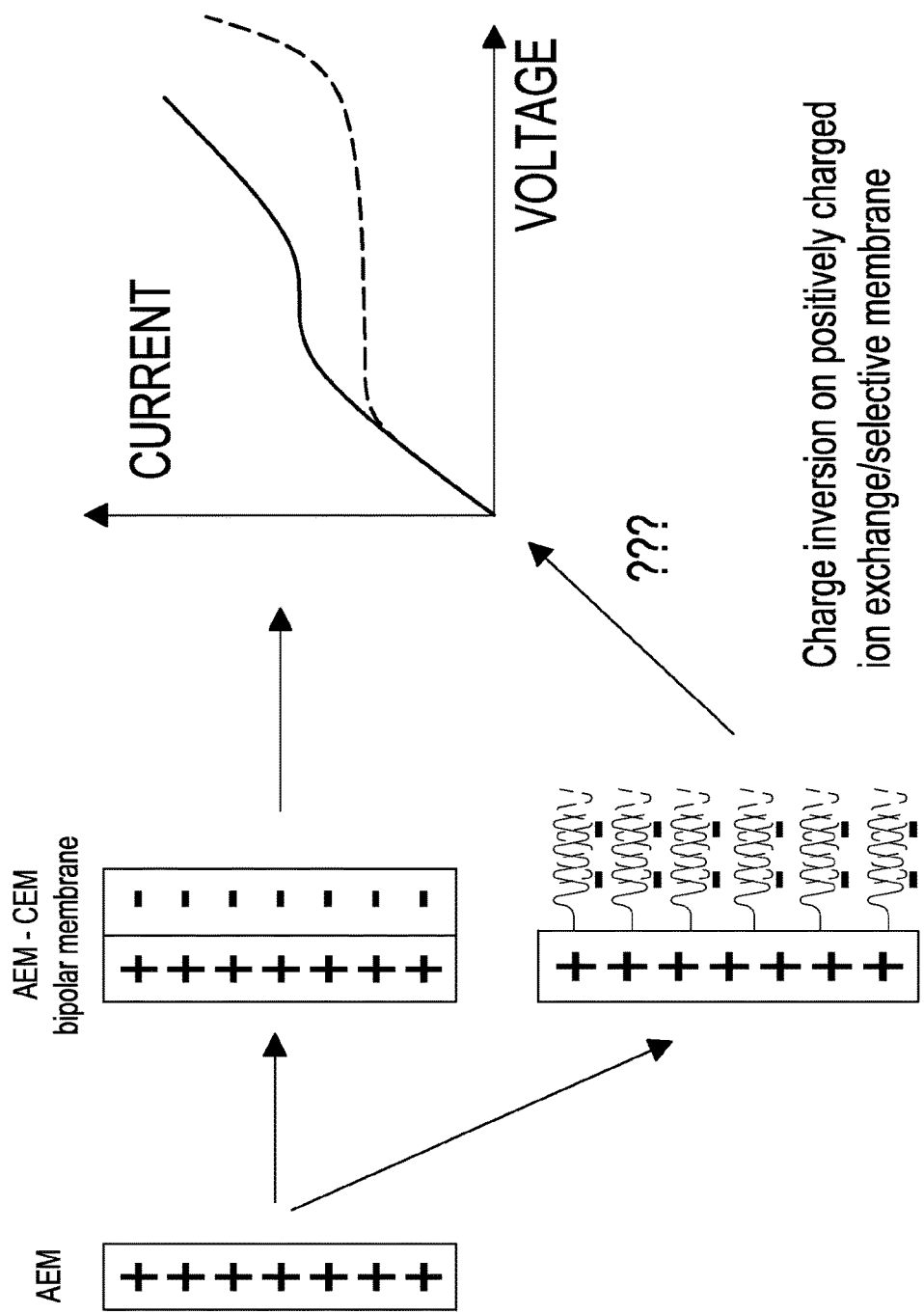
FIG. 6 depicts a current voltage curve for a single anion exchange membrane or an anion exchange membrane in combination with a cation exchange membrane.

The result is that one side of the membrane has an increase in ion concentration and the other side has a decrease in ion concentration. When measuring the current voltage curve (CNC) of this membrane, as shown in FIG. 6, the result is a non-linear characteristic CVC. It has three main regions, underlimiting, limiting, and overlimiting. The limiting region is associated with the formation of the depletion zone of the membrane. The overlimiting region is associated with the mechanism that destroys this depletion. If an anion exchange membrane is combined with either a cation exchange membrane or with nucleic acids, the curve shifts to the right, as shown by the gray curve. The shift in the curve is dependent upon the quantity and length of the nucleic acid. Thus, the quantitation and characterization of nucleic acids is possible through the determination and characterization of the current voltage curve.

Figure 7:
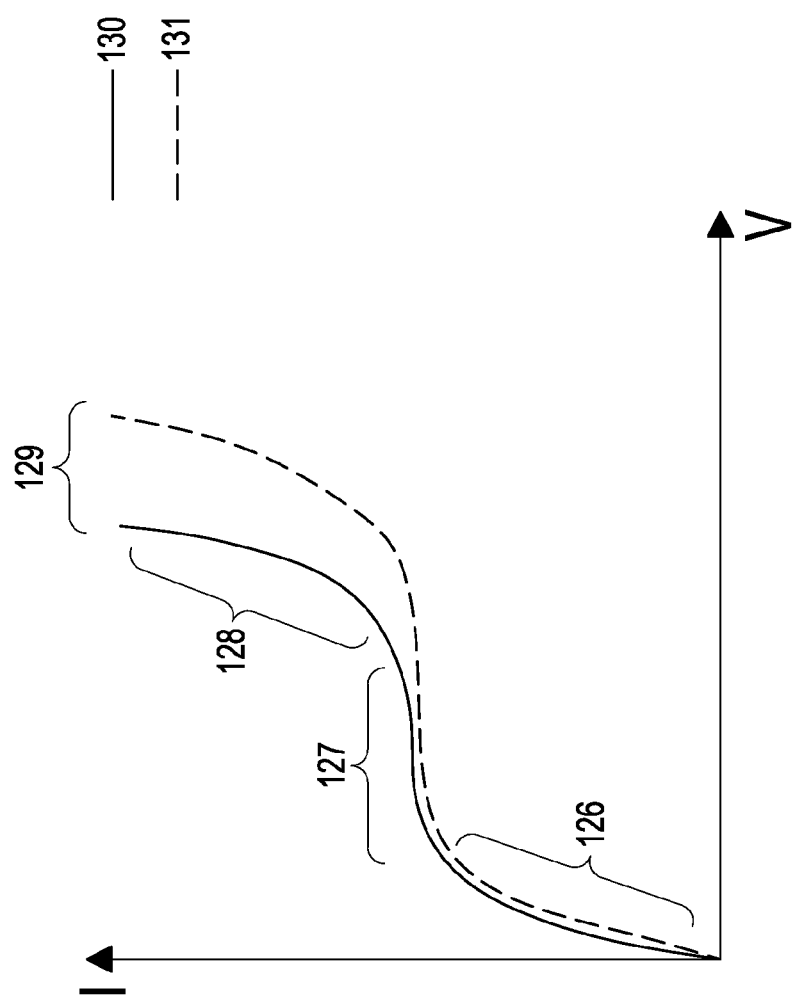
FIG. 7 depicts a chart of the current compared to the voltage, or the current voltage curve (CVC), including the signature regions of the curve. The solid curve represents the signal measurement prior to the addition of sample, and the broken curve represents the signal measurement following the addition of sample.

FIG. 7 emphasizes the specific regions of the current voltage curve. An initial linear region is referred to as the underlimiting region. The curve deviates from the linear direction in the middle of the cure, and is referred to as the limiting region. Finally, the curve rises again in a linear direction, and is referred to as the overlimiting region. The source signal must be constant for all the experiments completed. The source signal is the time between current increases and the amount of current increase each time period. In this way, the differences can be measured and charted in the CVC for each condition in the experiment.

For characterization and quantitation of the target molecule, the change in the voltage between the two curves is measured. Prior to the current being applied, negative molecules near the membrane will begin to absorb on the surface of the membrane. The anions near the membrane will move into the membrane as well. After the current is applied, then more and more negatively charged molecules will move towards the membrane.

Figure 8:
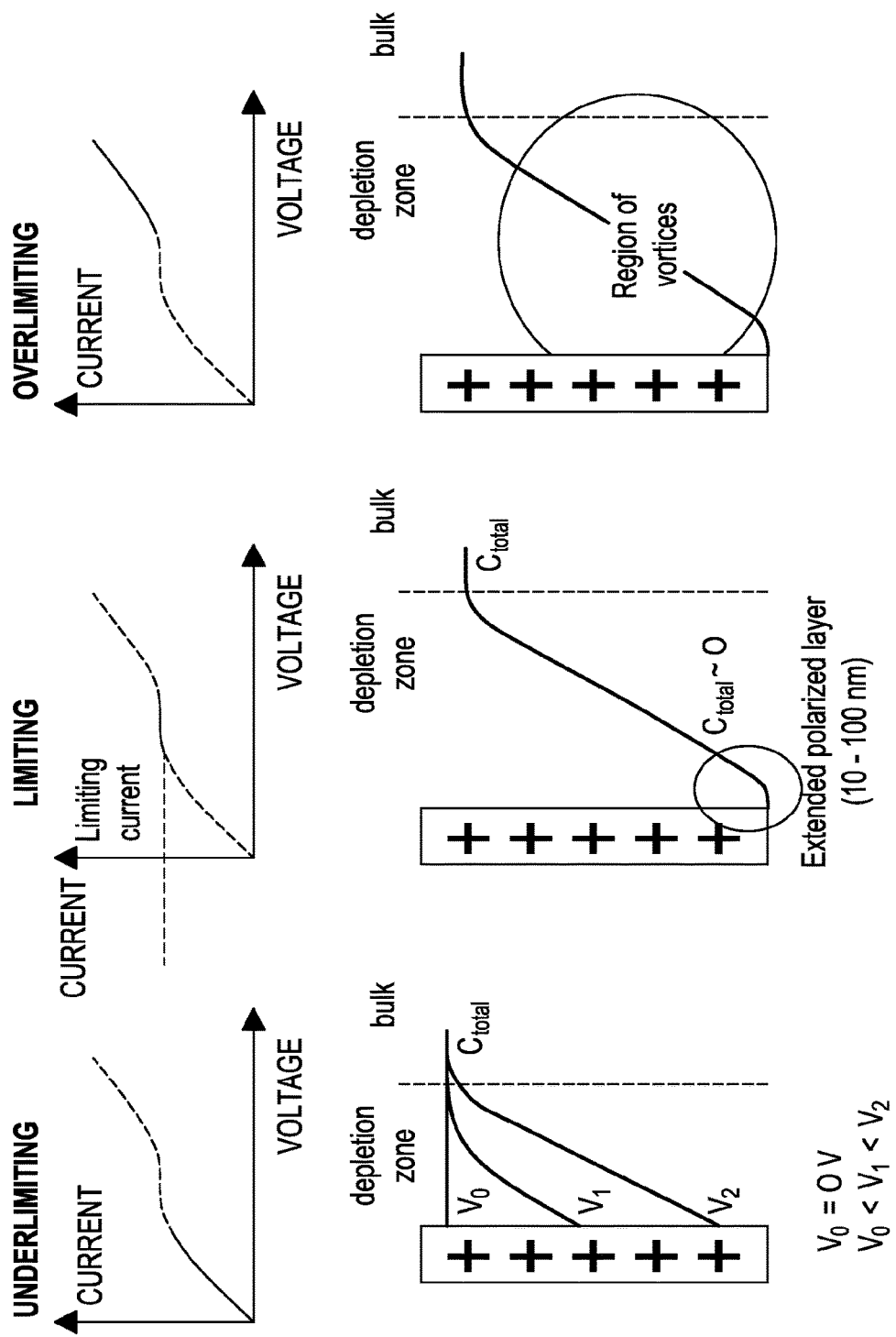
FIG. 8 details the various regions of a current voltage curve, including the under-limiting, limiting, and over-limiting regions (OR).

Initially as the voltage rises the negative ions move through the membrane creating a depletion zone. There are two phenomena that occur that cause the CVC to change from the underlimiting region to limiting region to overlimiting region. The first is microvortices and the second is water splitting. Both occur near the interface of the membrane, as described in FIG. 8. At the underlimiting region of the curve, anions move through the membrane and as these deplete the voltage increases across the membrane. The concentration zone is where the anions concentrate after moving through the membrane. There is a depletion, which means there is small number of ions that carry the current, which is associated with a high voltage drop. At some point, the concentration of the ions in the depletion zone will be close to zero. At this point more current cannot pass through the membrane. This is the beginning of the flattening of the CVC or the beginning of the limiting region of the CVC. At this point, there is a very high field which triggers motion in the electrolyte or a microvortice. When this happens the depletion zone is destroyed. The mixing brings new ions that are further away from the membrane to the membrane and then the CVC begins to rise in a linear direction again, and this is the overlimiting region.

The underlimiting region is when there is sufficient ions on both sides of the membrane. When there are sufficient ions on both sides of the membrane, then as the current is increased the voltage is also increased in a linear manner.

The limiting region is when the increase in the voltage is used to extend the depletion zone, which results in smaller changes in the current. The current does not increase or increases only very slowly—in other words there is a tendency to be constant.

The overlimiting region is when there is sufficient voltage in the system that the vortices start to mix the electrolyte and destroy the depletion region. At this point new ions, which can carry the current, are brought to the membrane, resulting in the final linear slop in the curve.

When nucleic acids absorbs to the membrane, the flux of the ions is changed. At the same time, the nucleic acids suppress the vortices. In the place of vortices is water splitting, as shown by the equation: $H_2O \rightarrow H^+ + OH^-$.

A small layer exists between the membrane and the nucleic acid absorption. The water molecules near the depletion zone are subjected to a high electrical force. This generates new ions as the water splits into positively charged hydrogen molecules and negatively charged $OH^-$ molecules. The result is an electrochemical reaction that separates the water molecules. The $OH^-$ molecules travel in the direction of the membrane whereas the $H^+$ molecules move in the opposite direction.

The permeability, or the size of the molecule that can travel through the membrane is about 200 g/mole in terms of molecular weight. Anything larger will not go through the membrane. DNA, RNA, microRNA molecules are therefore too large to pass through the membrane.

The rate of water splitting depends on the concentration of the targeted molecules. If there is a large concentration then the change will be more gradual than with lower concentrations. Consequently, the sensing has the ability to quantify the concentration of targeted molecules. The shift of the CVC from the baseline, or measurement without targeted molecules, to the CVC with targeted molecules has the ability to determine both whether the target is present and the amount of the target present.

When the concentrations of target molecules are low, the vortices are delayed slightly and there is some water splitting. When the concentrations of molecules are high, there are fewer vortices and more water splitting. As a result, different curves are measured and generated for different concentrations of target molecules, as is the case for nucleic acid target molecules. Thus, the further the shift of the CVC to the right the higher the concentration.

Figure 9B:
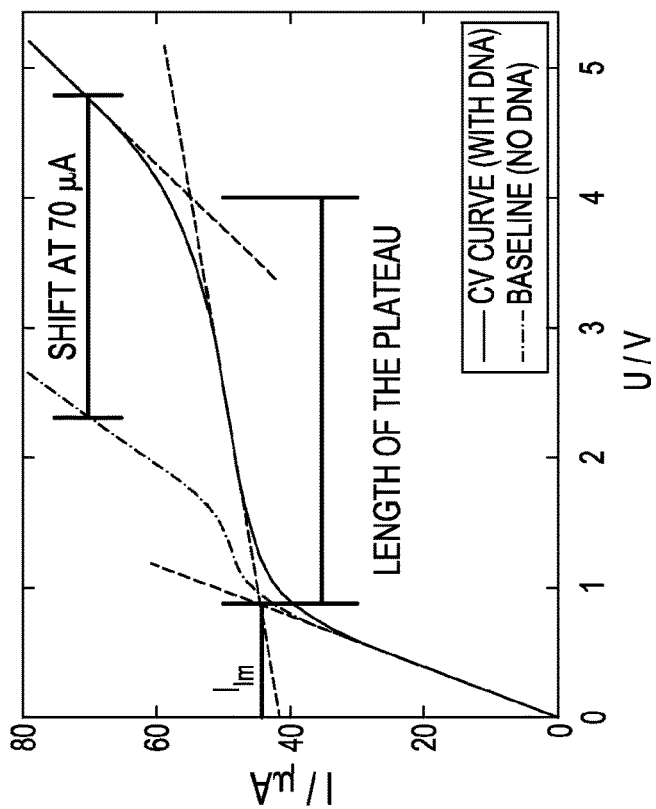
FIG. 9 shows the CVC characteristics with ssDNA samples at varying concentrations. There are distinct curves depending on the concentration of the DNA.
Figure 9A:
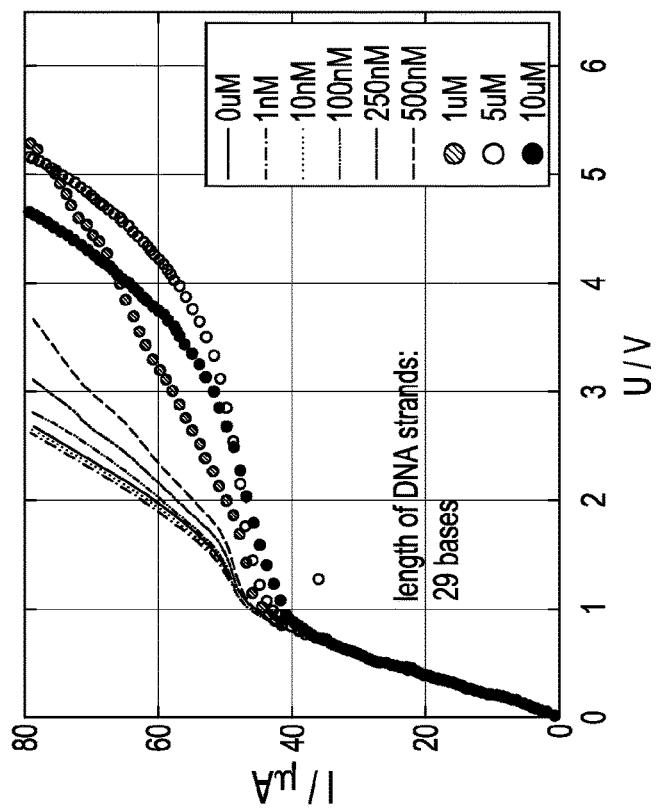

FIG. 9 shows the CVC characteristics with ssDNA samples at varying concentrations. There are distinct curves depending on the concentration of the DNA. Measuring the shift allows for quantification of the DNA. The baseline in this figure is measuring the CVC of only the membrane as the current is increased and the voltage is measured. The other curves show that as the concentrations of DNA go up, the curve shifts to the right. At first the curves of 1 nM to 500 nM share the same underlimiting region with the baseline measurement and a portion of the limiting region with most of the shift occurring in the overlimiting region. With increasing concentration of DNA the CVC continues to shift further to the right until a certain threshold, in this case 1 μM and larger, where the shift pattern changes and the limiting and overlimiting regions begin to shift back towards the baseline measurement.

Figure 10A:
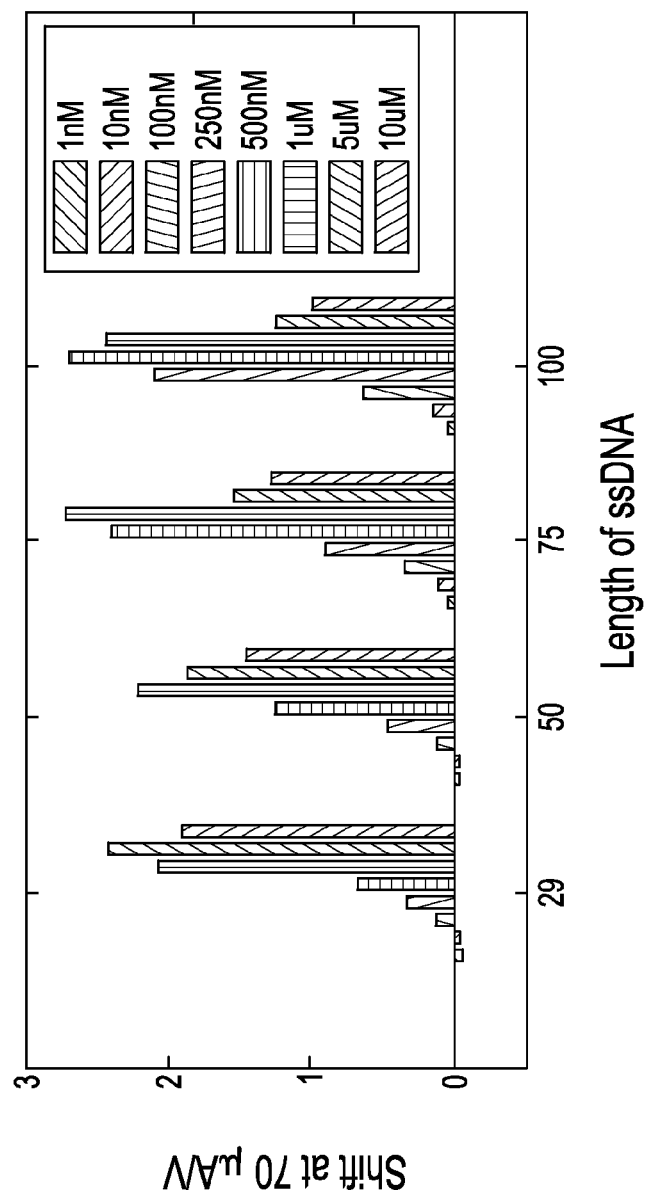
FIG. 10A shows a graph of the shift in measured voltage at a chosen overlimiting current as a function of the length of ssDNA given by the number of bases and various concentrations.

FIG. 10A graphs the shift length by the number of bases of ssDNA at each concentration. Each DNA consists of nucleotides that are linked together by phosphate groups. Each phosphate group is negatively charged. If a single sample is, for example 23 nucleotides long, then it has 23 phosphate groups that are negatively charged. However, the length of the nucleic acid is not important, but the negative charge born by these molecules is important.

Tf nucleic acids of different lengths are used with the sensor unit (for example, 29, 50, 75, 100, as shown in FIG. 10A) there are different concentrations of phosphate groups or a different number of phosphate groups on each. The original concentration of nucleotides is multiplied by the number of phosphate groups resulting in the concentration of phosphate groups in each sample. This can be plotted with respect to the shift at 70 microampiers in the graph in FIG. 10B, left. This shows as long as the target molecule is negatively charged, there will be a shift in the measurement. All the samples, even though they have different CVC shifts for concentration dependence, provide the same signal when the data is re-plotted with respect to the charge. Thus the nature of the molecules is not important, but rather, the charge and the concentration of the charge bound on the molecules. The charge is the parameter that governs the whole system of detection.

The graph on the right of FIG. 10B plots the slope of the over limiting region (OR) on the y-axis and the phosphate group concentration on the x-axis. For small concentrations of nucleic acids, there is a small shift in the CVC. With higher concentrations the limiting and over limiting slopes significantly. Most of the slope change was in the over limiting region. This charts shows that there are some mechanisms that suppresses the current causing the progressing shift in the CVC with larger concentrations. With more concentration of nucleic acids on the membrane more current is required to carry the same amount of voltage. If a critical concentration of nucleic acid is reached, then the current and thus the slope goes up again. Something else must be happening in order for this to happen and be seen in the shift in CVC. The graph links this behavior in the OR to the phosphate groups. As the concentration of nucleic acid increases, the vortices are slowly suppressed and the water splitting reaction slowly increases. Thus, everything that is given is based on the concentration of the fixed charge on the molecules.

Figure 11:
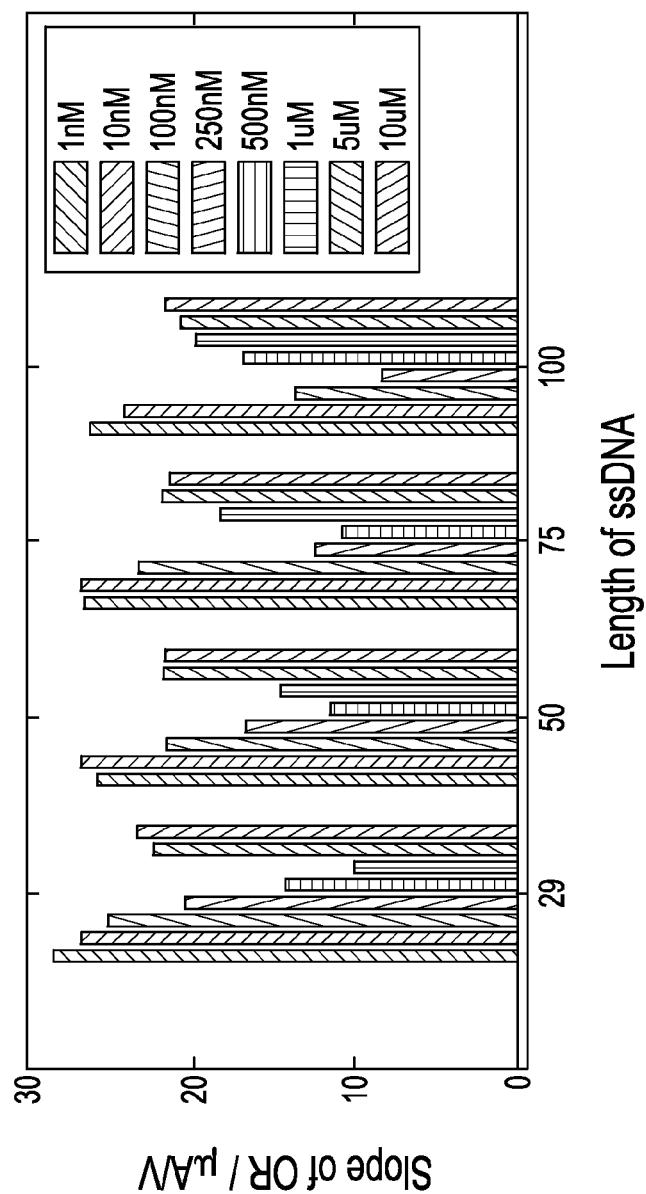
FIG. 11 shows a graph with the slope of the OR plotted with the ssDNA length to identify patterns.

FIG. 11 shows a graph with the slope of the OR platted with the ssDNA length to identify patterns. DNA with increased concentration results in a decrease in the slope, thus supporting the concept that two mechanisms are responsible for the over-limiting region, the vortices (electroconvection) at low DNA concentration and the water splitting at high DNA concentration.

The vortices as described above can be visualized with the system using rhodamine and fluorescein combined with the pH changes with increasing concentrations of DNA in the system. Using rhodamine, there are intensive vortices in the absence of DNA. With 1 μm concentration, there are some vortices before going away and with 10 μM the vortices disappear. Thus, with increasing concentrations of DNA, there is a loss of vortices near the membrane.

The visualization of fluorescein becomes greener with an increase in pH over 6. If the pH is low then the color disappears. When there is no DNA, the green is constant. With 1 μM DNA, a black region develops from the membrane and extends into the channel. For 10 μM DNA, this black region develops much faster and goes much farther into the channel. Thus, with increasing concentrations of DNA, there is increased water splitting reaction that changes the pH levels of the solution. This is the explanation of the occurrence of the $H^+$ ions.

In addition, the sensing unit is capable of sensing specific targets, such as viral DNA or microRNA, which makes it possible to detect diseases, genes, and other applications for detecting genetic material. Current technologies, such as microarrays are passive in that the sample is placed on the microarray and then there is a waiting period for the molecules to hybridize on the sensors. In addition, there are multiple washing steps and then fluorescence is used to see visually if there was hybridization. Thus, current technologies, such as microarrays are passive because there is no mechanism or system that can accelerate the movement of the molecules or the separation of the target molecules.

The sensor unit disclosed herein allows for hybridization and measuring the hybridization with the shifts of the CVC instead of fluorescence. Because the anion and cation exchange membranes cause vortices, these can be used to mix the molecules near the sensor to accelerate hybridization. In addition, a field that is created with these membranes will allow a system to move, separate, concentrate and hold molecules in a desired location within a system. No mechanical force is necessary to complete all of these tasks automatically.

Longer sequences of nucleotides translates to more material on the sensor and this creates a larger shift in the CVC than probes with few sequences at the same concentration.

Reducing the size of the sensor, means that fewer molecules are required to hybridize to see a shift in the CVC. Thus, with a smaller sensor there is a greater ability to detect target molecules in smaller concentrations. In one embodiment of the sensor, the area is 1 $mm^2$ and has the ability to detect the target at 1 pM concentration with a CVC shift of ~0.15 V. In another embodiment, the sensor membrane has an area of 0.76 $mm^2$ and has the ability to detect the target at 1 pM concentration with a CVC shift of ~0.5 V. In another embodiment, the sensor membrane has an area of 0.049 $mm^2$ and has the ability to detect the target at 1 fM concentration with a CVC shift of ~0.75 V. In yet another embodiment, the sensor has two membranes with different surface areas to allow for a greater dynamic range of 1 fM concentration to >1 μM concentration of the target. There is a range of detection for each membrane area size such as 1 pM to 1 uM with 0.76 mm$^2$ or 1 fM to 100 nM with an area of 0.049 mm$^2$. There is a change in how much of a CVC shift there is for each concentration for each membrane area size, as described in FIG. 12.

Oligoprobes for Specific Detection

In some embodiment of the disclosure is a sensor unit that is capable of sensing specific target nucleic acids. Oligoprobes were attached to the membrane. In some embodiments, oligoprobes are small complementary sequences of DNA that are bound to the membrane and cause the specific target to hybridize to the probes, based on the complementarity of the oligoprobe to the target nucleic acid. The sequences required for specific targets are generally known, or can readily be ascertained. However, the process for binding the probes to the membrane makes the sensing with the membrane specific.

With the addition of the oligoprobes, all of the negatively charged molecules continue to migrate toward the membrane. However, only the target hybridizes to the probes. Washing buffers are used to remove any non-specific interactions on the membrane, thus washing away any molecule that is not the target. Hybridization and absorption occur concomitantly when a current is applied across the membrane. However, washing the membrane removes anything that is not hybridized to the probe. The concentrations of the washing buffers must be higher than the binding buffers, but what remains will give an accurate CVC shift to determine the presence and the quantification of the target molecule. The molecules that hybridize to the probe remain on the sensor, resulting in a shift in the CVC following the wash, if hybridization occurs. In the absence of hybridization, there is no shift in the CVC.

FIG. 6 shows a membrane with oligoprobes attached. Target molecules hybridize to the probes. Non-target molecules still absorb and are attracted to the membrane. However, the non-target molecules are removed when the membrane is washed.

The method of attaching probes onto an ion exchange membrane requires particular skill because the ion exchange membranes are chemically inert. Additionally, these membranes are typically used to remove ions from water, and are designed so that they are mechanically and chemically stable. Thus, for example, tradition methods of attaching probes to a membrane are inadequate. Thus, it has been surprisingly and unexpectedly determined that the inert surface of the membrane can be coated with a functional group. This method creates a permanent binding of the functional group to the inert membrane surface and importantly, maintains the attraction of the charge on the membrane surface. Briefly, and as described in Senapati et al., 2014, a membrane is exposed to UV radiation, whereupon photo-activated crosslinkers are immobilized on the membrane. The photoreactive crosslinkers are mixed with the oligoprobes, which are then immobilized as probes onto the membrane under UV radiation. If a 'wet' chemistry is used the reagents and chemicals can damage the properties of the ion exchange membrane. With the UV protocol only the surface is exposed to the reaction. Various molecules can be used as photoreactive crosslinkers, for example benophenone.

Figure 13:
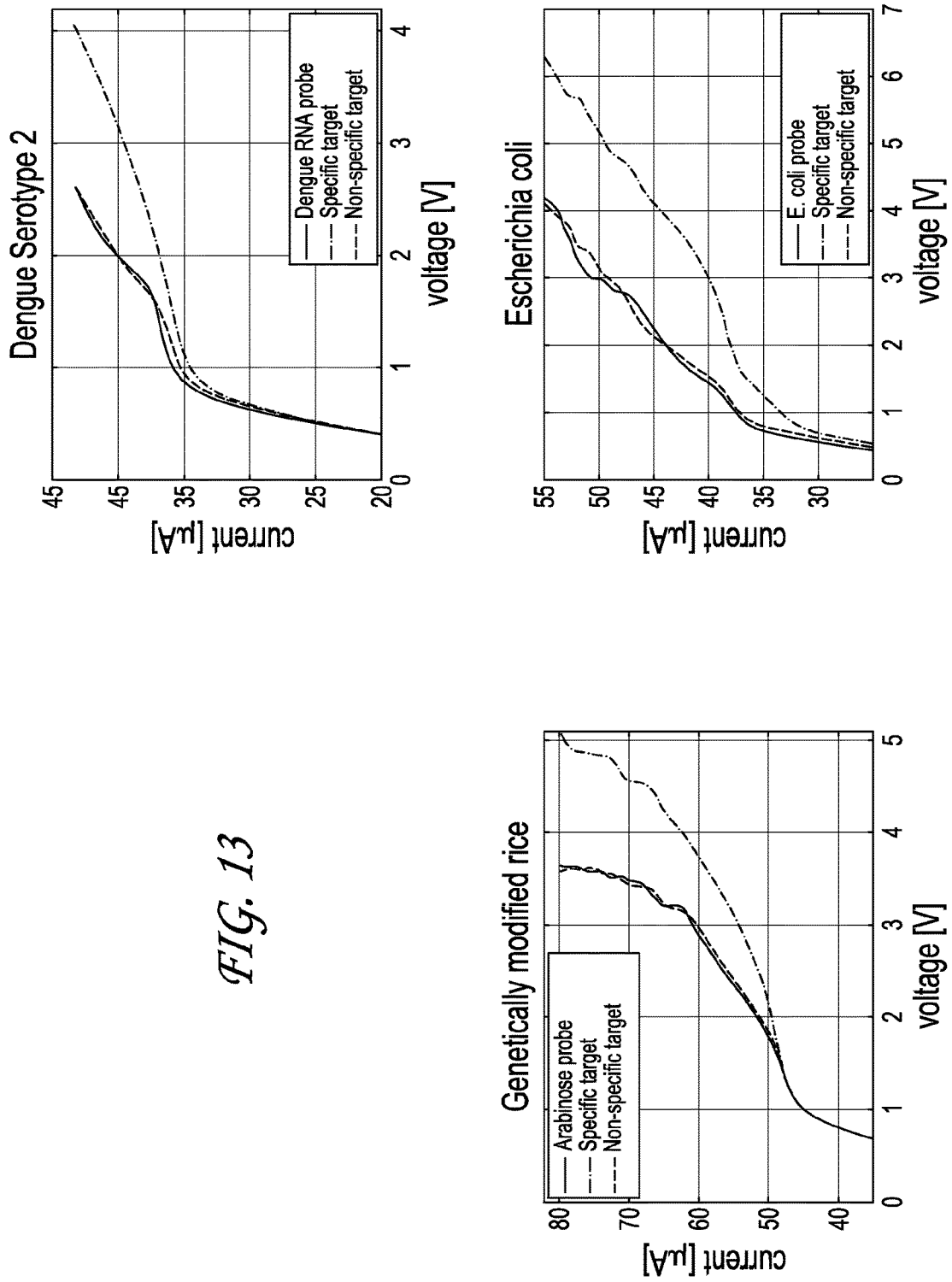
FIG. 13 shows the results of the nanomembrane based nucleic acid sensing platform for DNA coming from different samples FIG. 14 graphically illustrates the results of a test for dengue 2 virus, wherein dengue 3 virus was used as a non-specific control. The specific target (dengue 2) is capable of being identified from non-specific targets, with minute detection limits.

FIG. 13 depicts graphical representations of the results of detection and quantitation of various target nucleic acids. Various probes were immobilized onto the membrane, as described above. These probes include, for example, arabinose, dengue RNA, and *E. coli*, respectively. Samples were subjected to the membrane, wherein the samples contained both the target molecule and also non-specific molecules. Following the wash step, the only samples containing the specific target showed a shift in the CVC profile, as shown. Thus, when arabinose was present in the sample, the membrane having arabinose probe immobilized thereon showed a shift in the CVC profile. Likewise, when dengue RNA was present in the sample, the membrane having dengue RNA probe immobilized thereon showed a shift in the CVC profile, and the membrane having *E. coli* probe immobilized thereon showed a shift in the CVC profile when *E. coli* was present in the sample. However, when the specific target was not in the sample, for example, when non-specific target was in the sample, there was no shift in the CVC profile following the wash step. As is readily apparent to one of skill in the art, the above detailed assays are not limited to the specific targets described, but can be expanded to include any number of specific targets of interest, by immobilizing a probe to that target onto the membrane. These studies showed that the sensing unit alone is capable of detecting a target molecule down to a concentration of about 100 nM.

In some embodiments of the microfluidics sensing unit, the unit is a small, reproducible unit. In some embodiments, a hollow polyethylene screw is inserted onto a rubber o-ring with the sensor beneath. The hollowed out area provides for the reservoir for the electrolyte and electrodes. The substrate with a fluidics channel has two openings, one the inlet and the other the outlet. These opening also provide space for the electrodes to apply and measure the current.

In some embodiments of the sensing unit, a software system is provided for measuring the current. In some embodiments, the software system is Gamry software, which records the measurements and displays the results of the CVC on a graph. As will readily be apparent to one of skill in the art, any typical measurement, display, or readout systems and techniques may be used while staying within the scope of the invention.

In some embodiments of the sensing unit, a particle sensor is employed to increase the sensitivity of the sensing unit. The particles are responsible for allowing the detection capabilities of charged molecules. The detection limit of the ion resin particle sensor lies between 100 pM and 10 nM, depending on the coverage of the particle with the probe and its availability for hybridization. In some embodiments of the particle sensor unit, the detection limit is lower than the detection limit for the ion exchange membrane.

Figure 14:
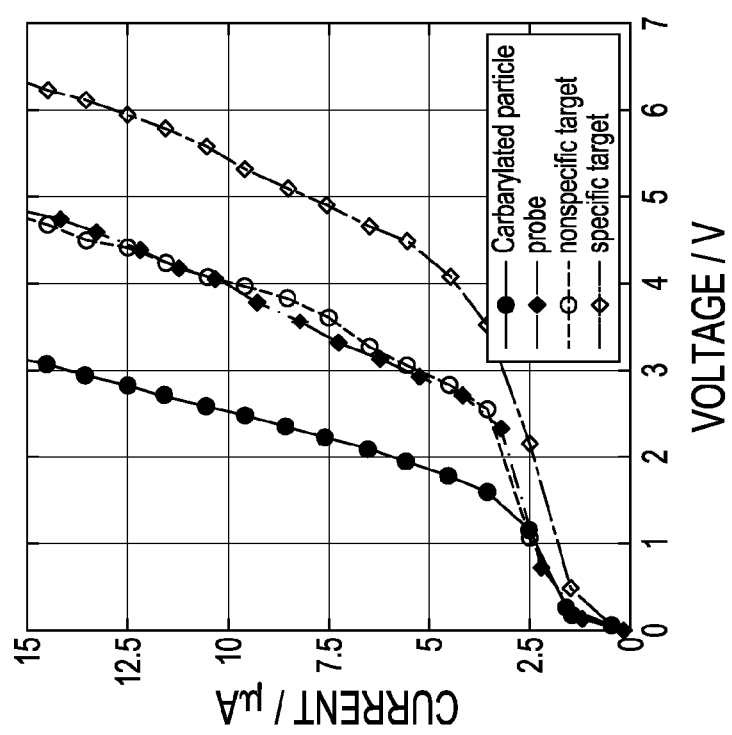

FIG. 14 shows the determination of the detection limits using one embodiment of the particle sensor. A oligoprobe against dengue 2 virus was immobilized on SBG1 anion exchange particles. A sample containing a non-specific target (dengue 3) and a specific target (dengue 2) was placed in contact with the anion exchange particles, and a detection limit of about 100 pM was determined.

FIG. 15 shows the testing of the membrane sensor with various concentrations of the same length of DNA and then eventually the testing of specific DNA for various diseases and crops. This shows that a specific probe could be attached with success for various types and lengths of DNA including plant DNA, virus, microRNA, or other nucleic acids.

Figure 16:
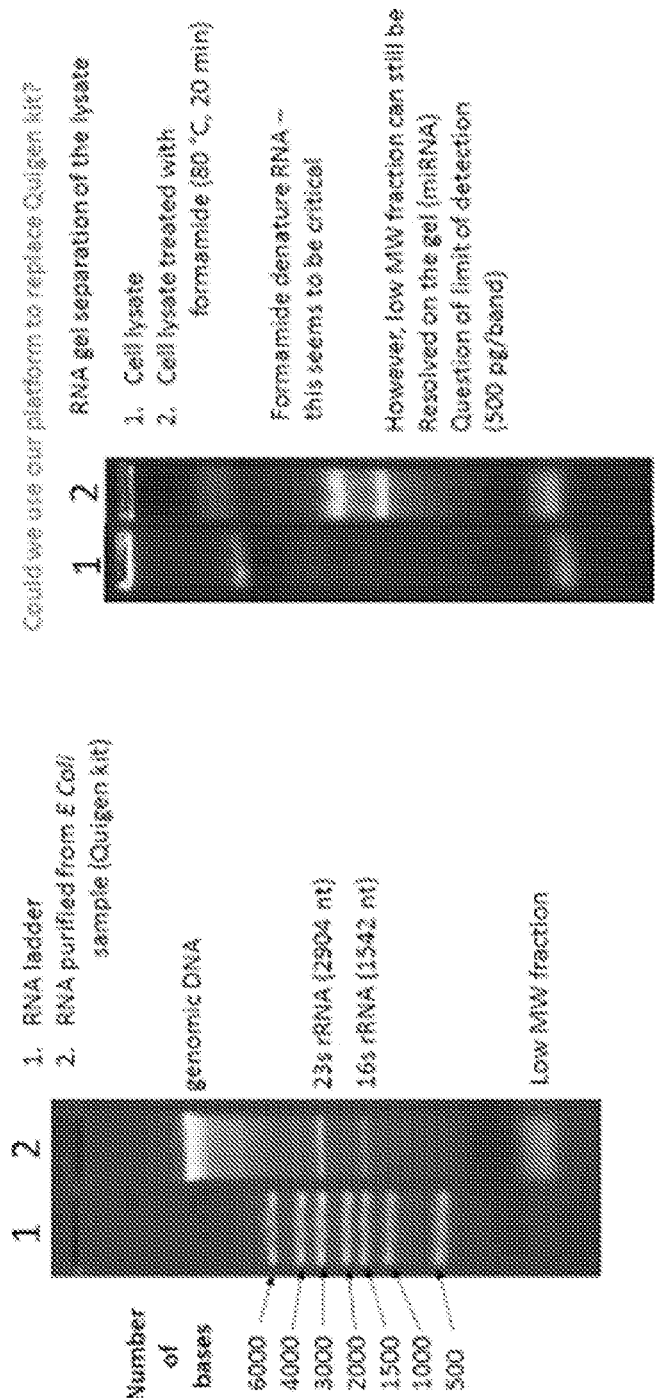
FIG. 16 shows nucleic acids within an agarose gel, demonstrating the ability of an agarose gel to separate nucleic acids based on size.

FIG. 16 depicts an agarose gel, demonstrating that nucleic acids can be separated based on size within agarose gel. The longer nucleic acids having more bases move slower as they move toward the positively charged electrode. The first lane is the RNA ladder and shows the separation in agarose. The next lane shows the *E. coli* cells purified and run through the gel. The low MW fraction is dRNA and then other bases with the genomic DNA at the top. The right image shows that there is a need to lyse cells.

Batch Sensor

In one embodiment of the sensing unit, the sensing unit comprises a batch sensor—a passive system with CVC shift measurements for quantification of target molecules. This is passive and requires a purified sample to be placed on the sensor and waiting for some time for the molecules to travel to the sensor and hybridize on the probes, or without a probe, to move to the sensor and test for a change in the level of molecules. Washes occur before measurements but after hybridization. The protocol is similar to microarrays.

Figure 17:
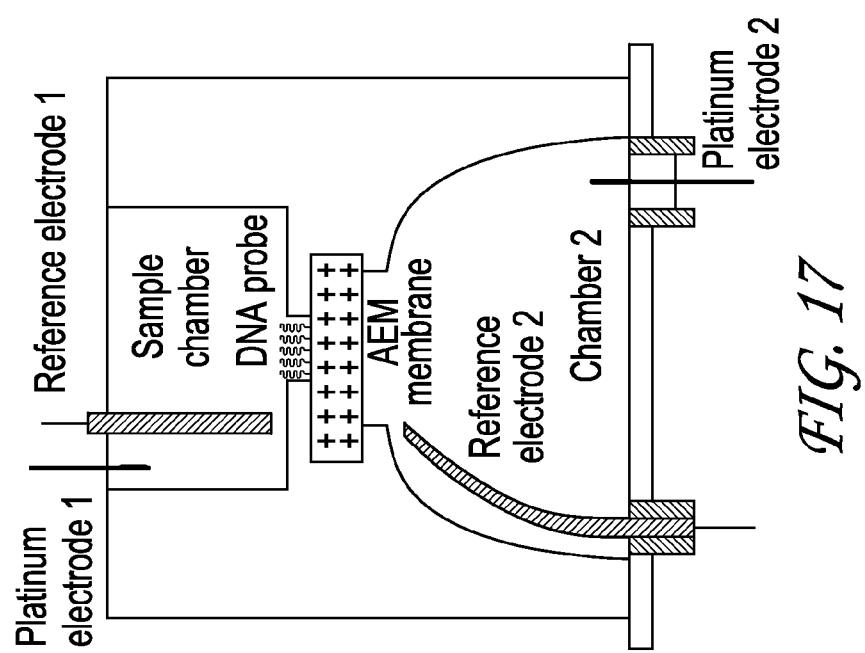
FIG. 17 depicts the placement of the pair of electrodes within the sensor unit to generate a circuit, wherein the electrical circuit has two electrodes to provide the current and two electrodes to measure the voltage.

FIG. 17 depicts one embodiment of the sensing unit comprising a batch sensor, wherein the batch sensor comprises an electrical circuit, which has two electrodes to provide the current and two electrodes to measure the voltage. In one embodiment, the reference electrodes are 3 mm apart in the batch sensor. However, the closer together the reference electrodes, the more sensitive the CVC is to the presence of molecules. On the other hand, touching is too close. Thus, the distance between the electrodes can be optimized, although various distances allow for proper functioning.

PCR Sensor

In some embodiments of the sensor unit disclosed herein, the sensor is used without probes and/or as a part of a polymerase chain reaction (PCR) system. In such embodiment, the sensor unit is still capable of determining some information about the amplification of genomic material. PCR amplifies genomic DNA into large number of copies and the membrane can be used to sense the change in the CVC after the amplification compared to the CVC prior to the amplification. This informs the user that the target exists and is useful in binary decisions as to the presence or absence of the target. The sensor unit is therefore capable of replacing the fluorescence and other detection techniques typically employed in PCR systems. Therefore, the use of the sensor unit in PCR systems can reduce the time and cost of typical PCR assays.

Integrated Sensor

In one embodiment of the sensor unit, the sensor unit is designed to sit on a fluidics channel and for the integrated system with the pre-treatment unit and the pre-concentration unit. This has a small piece of membrane embedded in a resin and attached to a reservoir. The probes are functionalized on the membrane. This is then inserted into a fluidics chip for integration with other functional units and components.

Figure 18:
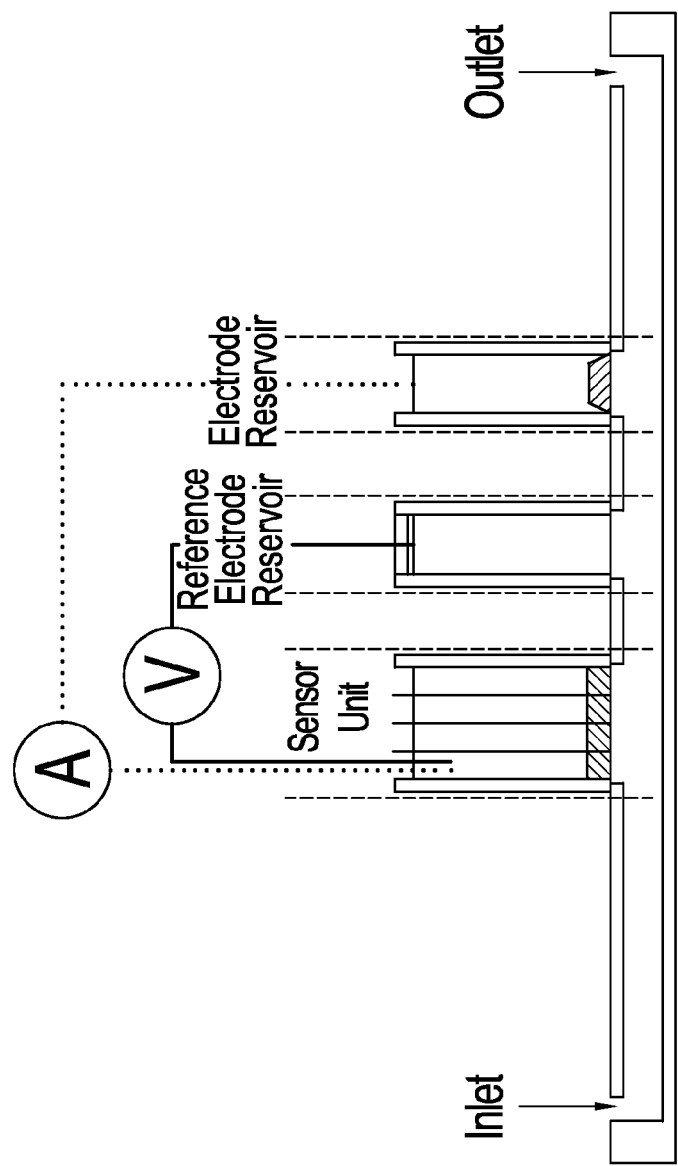
FIG. 18 provides a schematic representation of one embodiment of the sensing platform, wherein the sensor unit reservoir comprises two electrodes, one for applying the current and one for measuring the voltage.

FIG. 18 depicts one embodiment of the sensor unit, wherein two electrodes are located in the sensor unit reservoir, one for applying the current and one for measuring the voltage. Any placement of the electrodes will still allow the system to function, but it is better to have the electrodes as close as possible to the membrane embedded in the resin. There are two other electrodes, another reference electrode and an electrode to apply the current. The reference electrode can be in the fluidics channel (not blocking the flow, but in contact). At the location of insertion for this reference electrode, a seal is required such that there is no leakage from the channel and no entrance of air or other contamination of the system. The placement of the reference electrode in the channel needs to be as close to the sensor as possible. For example, the distance between the reference electrode and the sensor can be around 1 mm to 1.5 cm. Although the unit will function when the reference electrodes are 7-8 mm apart, the sensor unit displays increased sensitivity at shorter distances. Sensitivity of the sensing begins to suffer beyond 1-1.5 cm in distance. The system will still function at a greater distance between reference electrodes and will be more sensitive and function with the reference electrodes closer together. The sensor is more sensitive with the reference electrode in the channel as close to the membrane as possible. This will give a more sensitive measurement for shifts in the CVC when the signal has less distance to travel.

If the reference electrode is placed after the sensor. The limitation on the placement of the reference electrode in the channel is that the molecules may move towards the electrode and not the sensor when other units of the integrated chip are functioning in the separation, localization, and concentration of the molecules. It is best to have nothing between the point of entry of the molecules and the sensor unit to keep all the molecules from being stuck, absorbed, attracted or lost in their movement toward the sensor.

In some embodiments of the nanomembrane based nucleic acid sensing platform, the current applied is from 0 to 100 microampiers. This corresponds to the voltage of 0 to 22V. For the measurement it is from 0 to ~10V. However, one of skill in the art will readily recognize that these values are exemplary and are not intended to be limiting. For example, the aforementioned values are ideal for microfluidic devices. Nevertheless, when larger membrane sensors are used, larger current must be used to obtain the three regions of the CVC. For a smaller membrane less current is needed to get the three regions of the CVC.

When applying the current to gather the voltage measurements, the entire current progression must be completed without stopping the current. The step up in the current occurs and is held for a period of time then the current steps up again, all unbroken. The step up in the current and the time between measurements can be adjusted (so long as the baseline measurement and the final measurement are the same step up in current and the same time between measurements). The reason for this is because when the underlimiting region is created and moves ions. This cannot be interrupted or the measurement will not be reliable. The conditions in the channel must also be the same during the baseline measurement and the final measurement with PBS concentration. That is why it is important as well to make sure the underlimiting curve is the same for the baseline and the final measurement to make sure that any shift in the CVC is related to the change on the membrane sensor and not because of changes to the environment.

In some embodiments of the nanomembrane based nucleic acid sensing platform, the electrolyte used in the sensor reservoir is 100 microliters of 01×PBS. This will function as long as the electrodes are submersed. Additional volume will also function. A higher concentration of electrolyte means that a greater current is needed to measure the voltage. For 1×PBS there would be a need for 200 mA and this would take too long. Also, the more current that runs through the membrane, the greater the likelihood that something will be missed in the measurement or de-hybridization on the sensor or other damage to the system. Good conditions for hybridization need to be maintained, and this may require some compromise in the system. If 0.01×PBS is used, then the underlimiting region is difficult to measure and is often not visible. However, it will function at lower and higher concentrations.

In some embodiments of the nanomembrane based nucleic acid sensing platform, 0.1×PBS is used in the channel as well so that the area of greatest resistance is the membrane sensor. This means the measurement is for what is on the sensor. Sufficient electrolyte is needed in the channel to carry ions that carry the current. In a small channel with a large membrane, no CVC could be measured. The limiting region in that case is the electrolyte in the channel. All the voltage and the ions used to carry the current were used up by the channel. The channel must be large enough to carry the ions to carry the current and a small enough membrane so that everything that is measured is associated with the membrane. In some embodiments of the microfluidics channels, the dimension of the channel is 0.25 mm in height and 2 mm in width, which allows for enough ions to carry the current but is not the largest resistance for the current. By varying the size of the anion exchange membrane and the channel, some changes can be made that keep the membrane sensor at the greatest resistance.

In some embodiments of the sensor unit, a platinum electrode is placed sequentially on the opposite side of the reference electrode in the channel from the sensor. It is placed in a reservoir with electrolyte fluid and the reservoir has a layer of agarose gel that separates the reservoir from the fluidics channel. The agarose gel is given greater mechanical stability from supports (a screen) with porosity to allow the current to still pass through the channel. Pore size is about 200 nanometers in the gel. This reservoir may be an open or a closed reservoir. This agarose gel layer is to keep the reservoir separate from the channel to prevent the electrochemical reactions from this source electrode from affecting the conditions in the fluidics channel such as pH balance or bubbles and to make sure no flow between the channel and the reservoir.

Minimizing the distance between the two source electrodes is ortant, but not as important as minimizing the distance between the two reference electrodes, though both are important.

The environment in the channel needs to be the same when taking the baseline measurements of the CVC as when the CVC measurements are taken after hybridization and washing.

Multiplex or Multiple Target Use of Sensor

There are several ways to detect more than one target including having several membranes in a sensor, each with their unique target or probe. There can be a series of sensors along a channel whether multi-target or single sensors. Or the channel can divide to lead to sensors in series or a single sensor whether those are sensors with one probe or multiple probes. Additionally, there can be several integrated chips with their own targets on the sensor, as shown in FIG. 19.

Additional Units to Enhance Sensor

During the development of the sensor unit, all the testing was done with purified samples on a range of purposes, such as dengue fever, *E. coli*, and microRNA. However, when using an unpurified or real sample, the sensor unit alone does not perform to satisfactory levels. Thus, when using real samples, there are many components of the cell lysate that need to be separated from the sample in order for the sensing technology to work on unpurified samples.

In a real sample from a cellular lysate, for example, there is a conglomerate of cells, debris, and other matter. Also, to gain access to the target ssDNA additional treatment chemicals are often needed. However, such chemicals cannot come in contact with the sensor; otherwise, the chemicals can damage the probes and limit hybridization. The cells therefore need to be separated from the chemicals or lysing agents before they are brought to the sensor.

Thus, in addition to a sensor unit, additional components are used in the integrated chip of the nanomembrane based nucleic acid sensing platform. Thus, the integrated chip additionally comprises a pre-concentration unit and a pre-treatment unit. These units, in combination, purify the cellular lysate, isolating the targeted components. This allows for testing real samples using the sensing technology, but having an integrated system for purification, separation, filtration, isolation, localization, and concentration of the targeted components.

In some embodiments of the integrated chip, with both the pre-treatment unit and the pre-concentration unit, the ion exchange membranes are incorporated because of the phenomena they produced as part of an electrical circuit. When a current is applied, vortices and electrical fields are created. The field is focused within each of the two systems to use the molecular charge as a 'handle' to move the desired molecules. The vortices create non mechanical means of localizing molecules at needed positions and a mixing effect that accelerates the hybridization of molecules on the membrane sensor. Additionally, flow in a fluidics channel is also used for transport of molecules and washing the membrane sensor to improve sensitivity and specificity.

Thus, the pre-treatment unit and the pre-concentration unit are effective at moving molecules to any location needed, whether that is based on the position of the sensor to decrease time needed for sensing, or for other purposes in moving or holding molecules within a system.

The pre-concentration and pre-treatment units offer several advantages over traditional technologies. For example, traditional lysing techniques require several steps to pull out the target molecules for sensing. The preparation and purification take several steps before moving the sample mechanically or manually pipetting and/or transferring the sample to the sensing equipment. The integrated chip, however, completes these steps automatically and efficiently using electrical fields without any mechanical or manual methods.

In other means of enhancing specificity, the wash process is important as the wash is applied through either pumping, flow, or other means. PBS concentration is used at higher concentrations before returning the environment to baseline levels for measurement. If too much concentration is used then the probes and hybridization is damaged, if too little is used then non-specific binding or other debris may remain on the sensor membrane.

Example I—Manufacture of an Integrated Chip

In some embodiments of the integrated chip, the integrated chip comprises a reference electrode, a source electrode, a reservoir, an anion membrane, a resin, a photoreactive benzophenone-3,30,4,40-tetracarboxylic acid (powder)—1 mg (measured on scale) in 10 µL of DI water maintaining a pH of 6-7, sodium hydroxide—solid pellet (Fisher Scientific 500 gm). The integrated chip is fabricated comprising a sensor disc, wherein once the sensor disc is out of the mold, measure I-V curve (same step up as when experiment is run, must be identical), a reservoir, an assembled sensor disc & reservoir.

Example II—Functionalization of the Membrane

The membrane may be functionalized as described previously. A functionalization of the membrane may be performed prior to sensor disc step or after assembly of disc and reservoir, however, it is better to do so after because there are fewer chances of contamination afterward. The membrane may be carboxylated by: 1) Dissolving 1 mg powder photoreactive benzophenone 3,3,4,4 in 10 µL of DI water; 2) Adding dissolved sodium hydroxide to achieve a pH of 6-7

(roughly 2 μL); 3) Placing a drop onto the membrane, let sit for 5 minutes; 4) Exposing to UV for 10 minutes, atmosphere in UV box in nitrogen (efficiency of reaction will increase with the gas); 5) Put in DI water and shake it to wash membrane, can use equipment to assist with this like a vortex, vibrating, or rotating machine; 6) Repeat last three steps two more times; 7) Leave in 0.1×PBS overnight. This swells the membrane; 8) Measure I-V curve (same step up as when experiment is run, must be identical). Expected that at least a 1 V shift in curve from bare membrane I-V measurement. If membrane is dry not conductive.

As is readily apparent to one of skill in the art, there are several other means of creating a chemical bond that prepares the probe for immobilization on the membrane. The anion membrane is inert and does not react with much, but there are other means that may be ascertained.

ExampleIII—Attachment of the Target Probe

Attachment of the probe to the functionalized membrane may be achieved as described herein. Following the prior I-V curve measurement, soak sensor unit in pH 3 for one hour. Following the one hour incubation: 1) Wash with 0.1×PBS; 2) Wash membrane surface with MES buffer (mixed at pH 5.5) three times, can use vortex machine, rotator, etc. for assistance; 3) Add 0.19 mg of or final mixture amount of 0.4 molar, powder (refrigerated, did not get name of chemical b/c camera did not focus); 4) Other chemistry will work to allow bonding of probe; 5) Leave drop for 30 minutes on top of 'dot' membrane area; 6) Leave inside some moist box/chamber so sensor unit does not dry out during the 30 minutes; 7) Wash with MES buffer; 8) Apply DNA probe with NH21 group (needs clarification), DNA probe modified with amine group; 9) Generally use 1 micromolar concentration of that DNA group in 0.1×PBS; 10) Put in the moisture chamber and leave overnight; 11) Wash with 0.1×PBS; and 12) Measure I-V curve (same step up process as entire experiment, must be identical).

If the I-V curve shift is not sufficient then the membrane should be discarded and the process started anew. If sufficient probe is not attached (meaning the curve did not shift enough) then the process was not done correctly or the probe did not attach sufficiently and the sensor unit will not measure properly, it will not have the appropriate sensitivity, the probe may be washed off during the chip process, or other similar errors.

Applications

As can be readily determined by one of skill in the art, the applications of the current probes on the sensor are numerous. For example, the sensor unit is capable of replacing fluorescence and other detection techniques of the PCR systems. Additional applications for the sensor may include, for example molecular detection and quantification such as: modular unit in the PCR process; plant testing; detection of specific genetic sequences; animal testing; human testing; environmental testing; or biodefense.

Pre-Concentration Unit

The functional overview of the pre-concentration unit is that molecules are transported within a fluids channel using the first electrical field or fluid flow from the pump unit. The first electrical field localizes and concentrates molecules at the sensor unit. A second electrical field blocks molecules from flowing beyond the localization area. The pre-concentration unit transports molecules in the fluids channel using the first electrical field. Also, flow in the channel from the pump unit moves molecules in the fluids channel. The first electrical field also concentrates and localizes the molecules at desired locations at the sensor unit. The second electrical field blocks molecules transported with flow from the pump. This prevents the molecules from being washed away beyond the desired location.

In one embodiment of the pre-concentration unit, two reservoirs filled with electrolyte fluid are housed in nonconductive tubes. These tubes are attached to a nonconductive substrate with a fluidics channel. The two reservoirs are separated from the fluidics channel by a cation exchange membrane (CEM) and uncharged gel plugs beneath the CEM. The uncharged gel suppresses vortices in the channel and near the membranes. Positioning of the two CEM membranes (one used as the auxiliary and the other as the pre-concentration membrane) along the channel served to localize and concentrate molecules between the CEMs. Trimethoxymethane is used to suppress the electroosmatic flow in the channel and also functions to seal the membrane.

Figure 20:
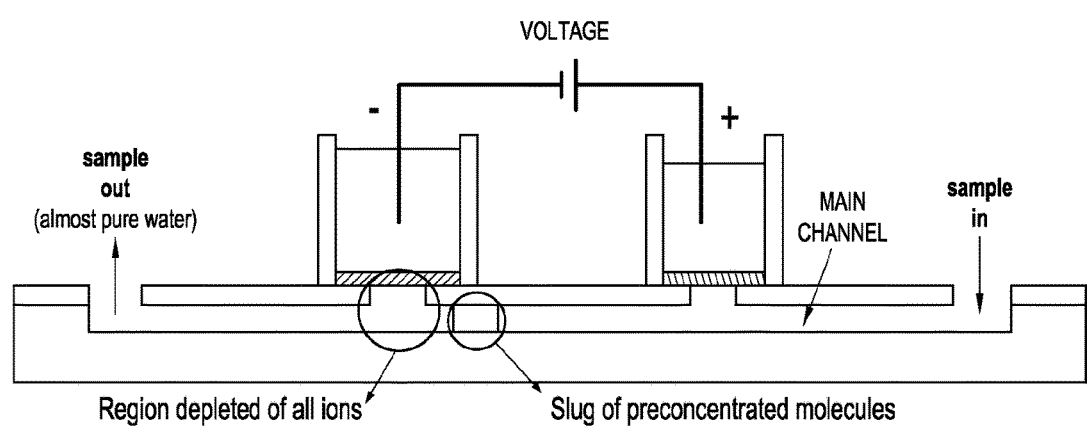
FIG. 20 depicts a schematic representation of one embodiment of the pre-concentration unit.

FIG. 20 depicts one embodiment of the pre-concentration unit. FIG. 20 shows the region depleted of all ions directly downstream from the slug of pre-concentrated molecules. The depleted region prevents large negatively charged molecules from entering. The position of the slug between the pre-concentration and auxiliary membrane is controlled by the set of flow rate and voltage applied. When the flow rate is too powerful it overwhelms the field. If the field is stronger, then it will adjust the placement of the slug. This allows for fine tuning placement of the slug.

In some embodiments of the pre-concentration unit, two CEMs are used to successfully localize and concentrate the molecules. If the auxiliary membrane is replaced with agarose gel then the molecules localize in the gel. If the agarose gel is used for the concentration membrane then there is no concentration at all.

Figure 21:
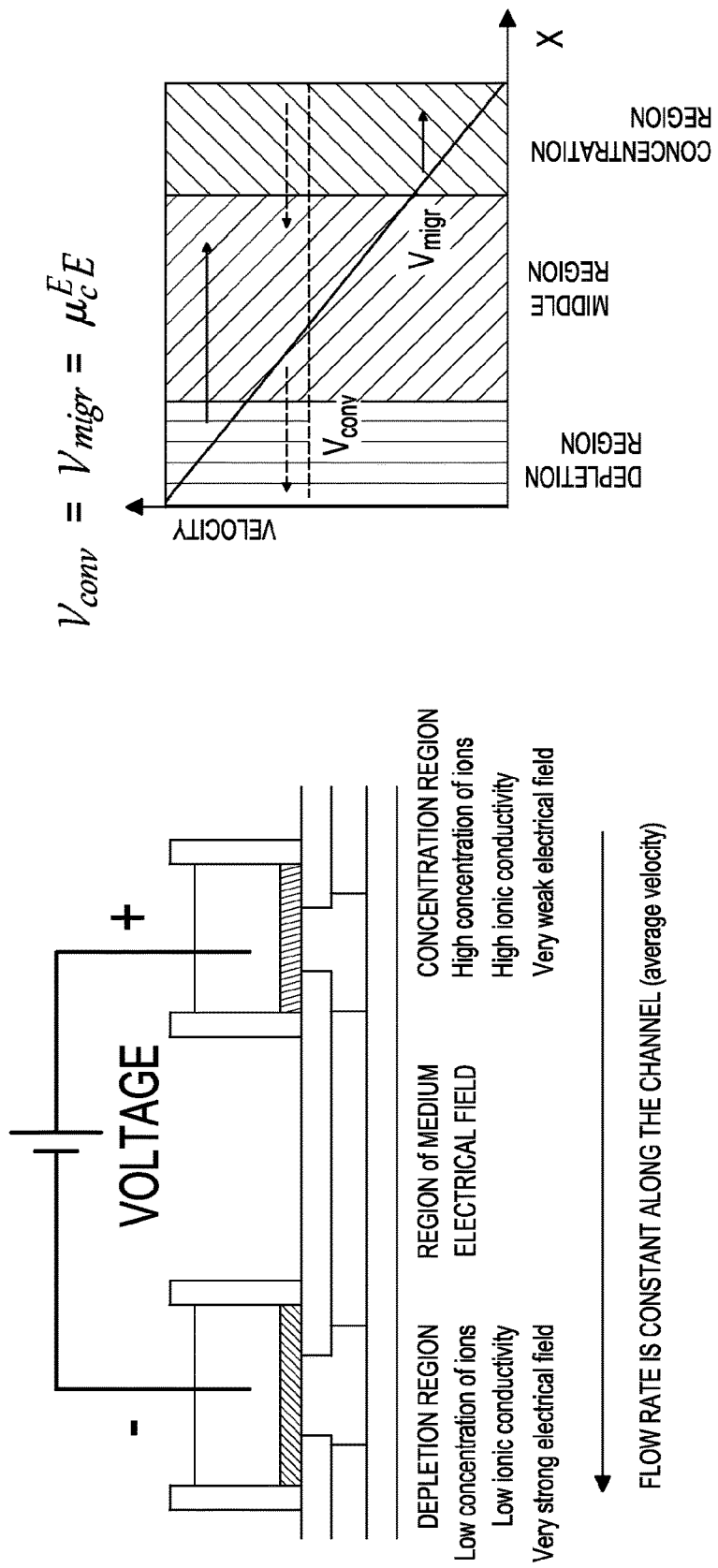
FIG. 21 is a schematic representation of the mechanism of pre-concentration. The molecules will pre-concentrate when $v_{conv} = v_{migr} = \mu^E_c E$

As shown in FIG. 21, when voltage is applied to the system, the voltage has some profile inside the channel. There is a concentration region and a depletion region. The depletion region is defined by low concentrations of ions, low ionic conductivity, and very strong electrical fields. The concentration region is defined by high concentrations of ions, high ionic conductivity, and very weak electrical fields. The molecules will pre-concentrate when $v_{conv}=v_{migr}=\mu^E_c E$, as shown in the graph in FIG. 21.

Flow through the channel has variation of the electrical field along the channel. If two dyes are mixed the dyes move at different velocities. When the field is activated it will separate the two dyes.

With the pre-concentration unit, the field moves the molecules through the channel. The field can be used to move the molecules, but flow can also be used. The idea is to move the molecules to the sensor unit. Flow is the easiest way to transport anything in the channel. A pump is integrated into the chip and creates the flow through the channel. The molecules need to be stopped in the sensor region. An electrical field is created to counter balance the flow. This will stop the molecules at the sensor region and the pump creates flow. This requires calibration to determine the right level of electrical field force and the right rate of flow so that a counter balance occurs. Too much flow will overwhelm the field. Flow is the force acting in the direction of the sensor and the electrical field is the force acting in the opposite direction.

It is difficult to determine what force is needed to get the molecules at the appropriate position. Each should cancel the other out and need a balance. If the flow is increased then the field needs to increase.

The way to do this is to create a region where the electrical force is low and another where the force is high. This is done with a pair of membranes. These are at the bottom of the channel. These are cation exchange membranes, negatively charged. The negative molecules will not absorb because there is a strong electrostatic repulsion between the membranes and the negatively charged molecules. The positive ions will be pulled out of the channel with the current is applied and into the cation exchange reservoirs for each membrane in the pre-concentration unit system. The anions cannot go through the field and with the flow begin to accumulate. The negatively charged molecules also accumulate and in this way the system concentrates the target molecules.

The calibration of the field and the flow then allows precise placement of the concentrated molecules at a desired location. In the integrated unit this is below the sensor. Calibration may also be dependent on electrolyte concentration, pH level, and conductivity.

With the current applied, on one side there is very low field because there is a low concentration of ions as they positive ions move into the reservoir through the membrane. On the other side is a high field because of the concentration of the ions. This blocks the molecules being pushed by the flow and concentrates them against the high field area created by the large concentration of ions. The force of the field can be calibrated and adjusted inside of the channel depending on the use and application. It can act as a valve, a concentrator, and filter. The electrical field prevents the molecules from being washed out of the channel when flow is applied.

Preferably, the sensors are 1 cm apart and the molecules concentrated between the membranes. However, this may be modified to put the two CEMs very close and make the space were the molecules could accumulate very small. Eventually as the CEMs get closer, the field places the concentration of the molecules before both of the CEMs instead of between them. The current is ~100 V to achieve this effect. As the molecules travel through the channel there is very little force until suddenly there is a very high force. The flow rate is about 1 µL per minute with using 100 V.

Applications

As can be readily ascertained by one of skill in the art, the pre-concentration unit may be applied in applications other than the integrated chip, and in applications in addition to those described above. For example, the pre-concentration unit has applications of: moving or localizing molecules at specific locations and at specific rates; concentrating molecules at specific locations; blocking movement of molecules carried in the flow of a channel; and control of the movement of molecules.

Pre-Treatment Unit

In some embodiments, the pre-treatment unit is generally used to separate molecules of interest based on electrical charge and molecular weight—and may be used prior to concentration using the pre-concentration unit. Briefly, a sample is introduced into the unit. An electrical field moves molecules through a filter. Molecules are targeted by their size and charge. For example, negative molecules of a certain size are moved through the filter. The molecules are then transported and concentrate at a determined location.

Figure 22:
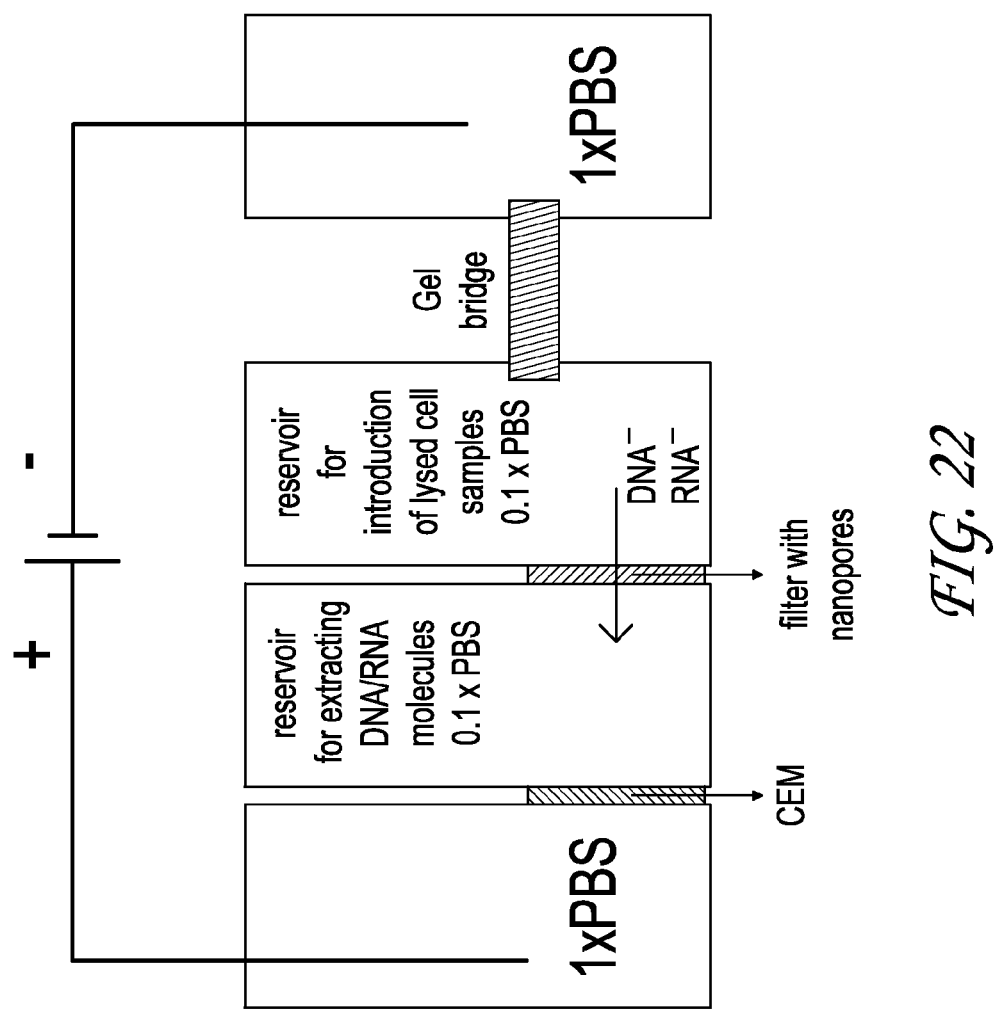
FIG. 22 shows one embodiment of the pre-treatment unit consisting of three reservoirs and integrating a nanofilter and cation exchange membrane

In some embodiments of the pre-treatment unit, the pre-treatment unit is used for extraction of nucleic acids, such as DNA or RNA molecules from lysed cells. This unit comprises three reservoirs and integrates a nanofilter and cation exchange membrane, as shown in FIG. 22. The working principle relies on the ability of nucleic acid molecules to migrate in the electrical field toward the anode and can be briefly described as follows: The sample with the lysed cells is pipetted into the first reservoir (sample reservoir) and the electrical field is turned on (polarity according to FIG. 22). All negatively charged molecules will migrate towards the positively charged electrode through the nanofilter into the second reservoir (reservoir for nucleic acid extraction). Because this reservoir is separated from the third reservoir with a cation exchange membrane, these molecules will remain in the second reservoir. Cellular debris, positive and neutral molecules will remain in the first reservoir. The extracted nucleic acid molecules can then be transferred from the second reservoir into the detection/pre-concentration unit by pipetting or alternatively, this pre-treatment system can be integrated within the detection platform.

In some embodiments, the pre-treatment unit extracts the target molecules by charge and size and localizes the molecules in a channel or in another reservoir. A single tube with an outer chamber with agarose gel layer at the bottom of the tube. This agarose gel serves to separate the chambers from the channel and the electrochemical reactions, bubbles, etc. There will be no direct mixing of the sample as well from the channel. Additionally, this layer of agarose gel allows the pulling or separation of molecules in the sample into the channel. Depending on the current charge either positive or negative molecules will be separated from the chamber into the channel through the agarose gel. The porosity of the gel can be modified to be larger or small depending on the need and thus also filters the size of the molecules that may pass through the gel into the channel. The gel also allows the electrical current to go through and the electrical field to flow through it. One of skill in the art would recognize that there are alternatives to agarose gel that are inert (holding no charge) and have the desired nanopore sizes and the mechanical stability.

The two outside chambers in FIG. 22 are for placement of electrodes and applying an electrical field through the system. Electrodes are inert material such as gold or platinum to prevent corrosion and permit continued reuse. The field moves negatively charged molecules from the reservoir for lysed cells into the reservoir for extraction. The gel bridge is in place to prevent electrochemical reactions from affecting the conditions in the lysed cell reservoirs. Also, the Cation Exchange Membrane (CEM) prevents electrochemical reactions as well in addition to preventing molecules from entering the reservoir on the far left of the diagram. The filter used has nanopores that filter molecules based on size. Thus, the system is designed to use electrical field and pore size to separate and filter molecules from one reservoir to another.

The sample is combined with chemicals to lyse the cells so that they are free floating in the sample. In some embodiments of the pre-treatment unit, the unit permits 100 microliters of sample to be processed in the tube. 10×TAE is added in the outer chamber as the electrolyte. An electrode is placed inside the outer reservoir and the other electrode is place in a reservoir for a cation exchange membrane. When the DC field is applied the molecules that have the charge will be pushed down the tube and depending on their size, will travel through the gel into the channel and toward the CEM. Because the membrane is the opposite charge of the molecules they cannot go through and concentrate near the membrane. This forms a slug of molecules, though some molecules are spread over the channel between the gel and the membrane. All the molecules that are the wrong charge or neutral or bigger than the porosity in the gel are held in the tube. In this manner, both the separation and filtration of the molecules occurs.

Figure 23:
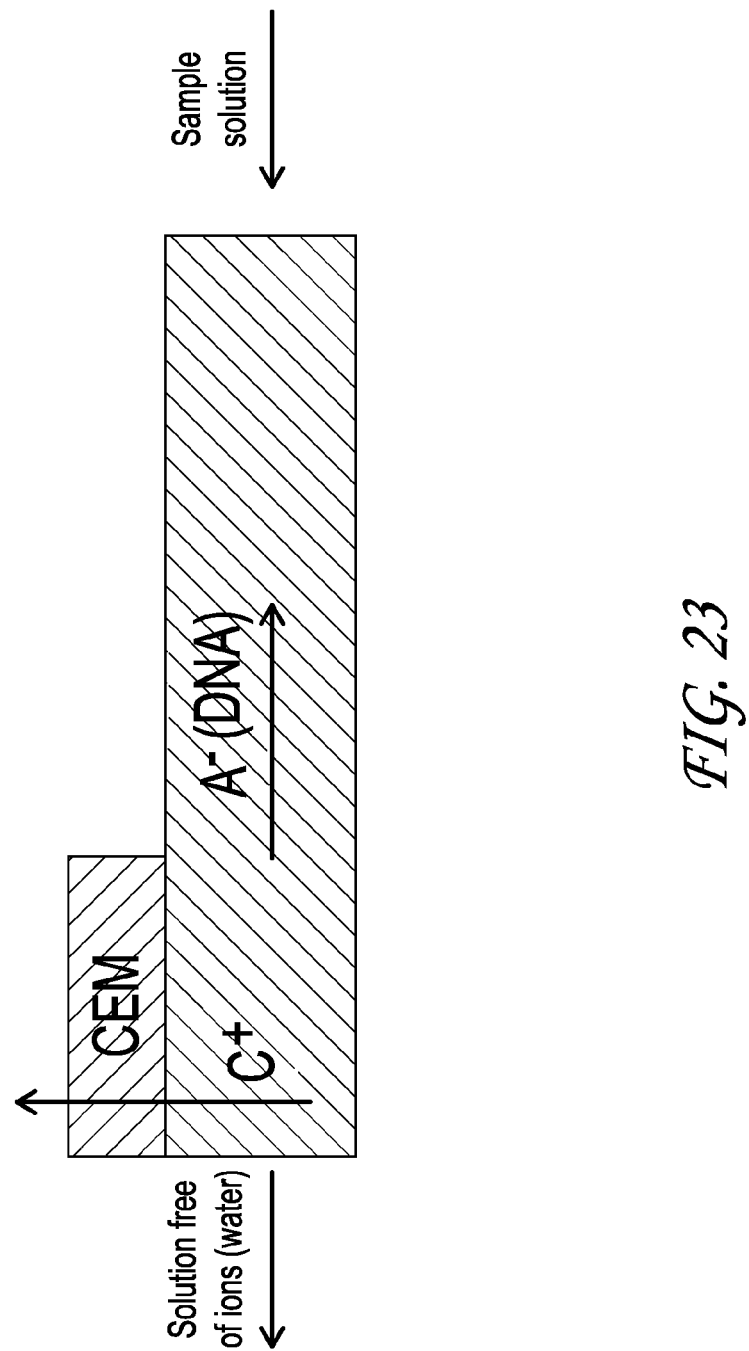
FIG. 23 shows the basic movement of ions caused by the electrical field in the pre-concentration unit.

FIG. 23 shows the basic movement created from the electrical field in the pre-treatment unit. Current through the membrane has to be high enough to quickly remove all counter-ions from the electrolyte beneath the membrane to create depletion. Co-ions will accumulate in front of the depletion region. To maintain the depletion the current has to correspond to the rate at which the ions are delivered into the depletion zone.

In some embodiments of the pre-treatment unit, the electroosmotic flow is suppressed by covering the nanofilter with UV curable gel. Because the filters commonly used have a positive surface charge, the negatively charged target molecules are attracted to the filter itself and remained stuck instead of transferring to the reservoir for extraction. Therefore, the nanopore filter was replaced with agarose gel that has a neutral surface charge, sufficient mechanical stability, and porosity. The added benefit of agarose gel is the ability to adjust the porosity based on the concentration of agarose used.

Figure 24:
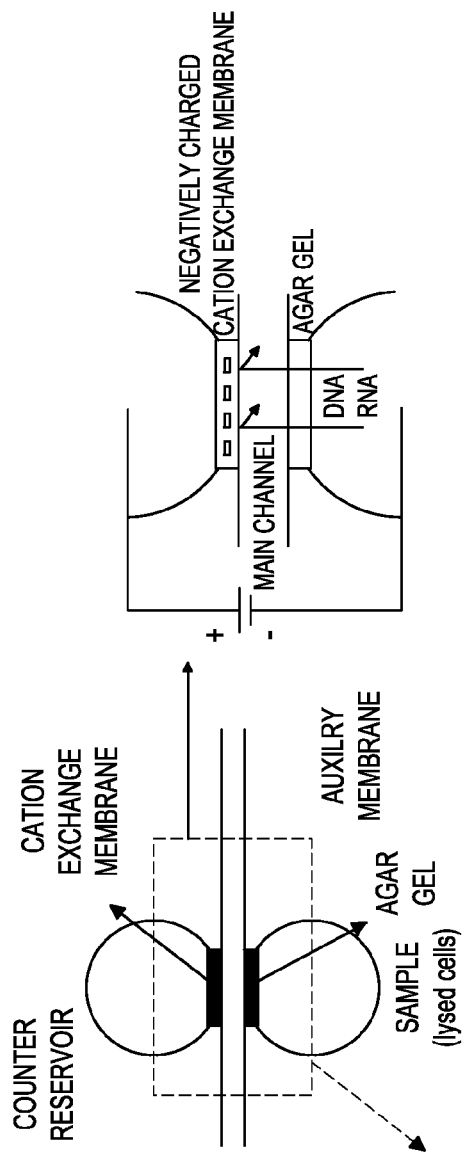
FIG. 24 depicts one embodiment of the pre-treatment unit, showing the extraction/separation of DNA/RNA molecules from samples.

Using an agarose gel filter layer, the pre-treatment unit system is capable of being used for samples containing a target single stranded DNA, for example, as shown in FIG. 24. The pre-treatment unit is integrated with the sensor unit in order to test specific single stranded DNA (ssDNA) targets using the membrane sensor with functionalized probes for the specific target. By running the sample through the pre-treatment unit, the CVC shifts measured on the membrane sensor provide a demonstration of the ability of the pre-treatment unit to separate and filter molecules.

ExampleIV—Pre-treatment Unit for Purifying Sample

The pre-treatment unit may be used with various lysing buffers for extracting DNA/RNA molecules from cells, such as human cancer cell lines, or from *E. coli*. The lysis buffers include: HCl solution (pH 2); NaOH solution (pH 13); a lysis buffer from Ambion cell lysing kit; DI water; and 1×PBS buffer as a negative control. The amount of obtained DNA, RNA and also proteins were determined from UV measurement. The amount of free DNA/RNA and proteins coming from samples lysed with HCl (pH 2), DI water and 1×PBS was very small. Moderate results were obtained for Ambion lysing buffer and very good results for sodium hydroxide.

In addition, the pre-treatment unit is used for ssDNA loading experiments where a DNA sample was pipetted into one reservoir (sample reservoir) separated from a second reservoir (loading reservoir) with a gel. After applying DC voltage (such as, for example 25, 50 and 75 V) on the system, the DNA migrated through the gel into the second reservoir. Every five minutes, samples were removed from both reservoirs and a UV absorbance was measured to determine the loading efficiency. For all voltages applied, the concentration in the sample reservoir went down and in the loading reservoir went up, as is observed in FIG. 25. The speed of loading increased with increasing voltage.

Lower voltage applied results in a longer time to complete the separation. At a higher voltage it takes less time. 10×TAE is loaded as the electrolyte in the CEM reservoir and in the electrolyte reservoir. In some embodiments, the system operates at 0.8 mA and 200 V. It will function with less but more slowly. At a higher voltage there is a risk of bubbles in the system. If too much current at too high of voltage creates heat and possibly bubbles for this electrolyte circuit.

Figure 26:
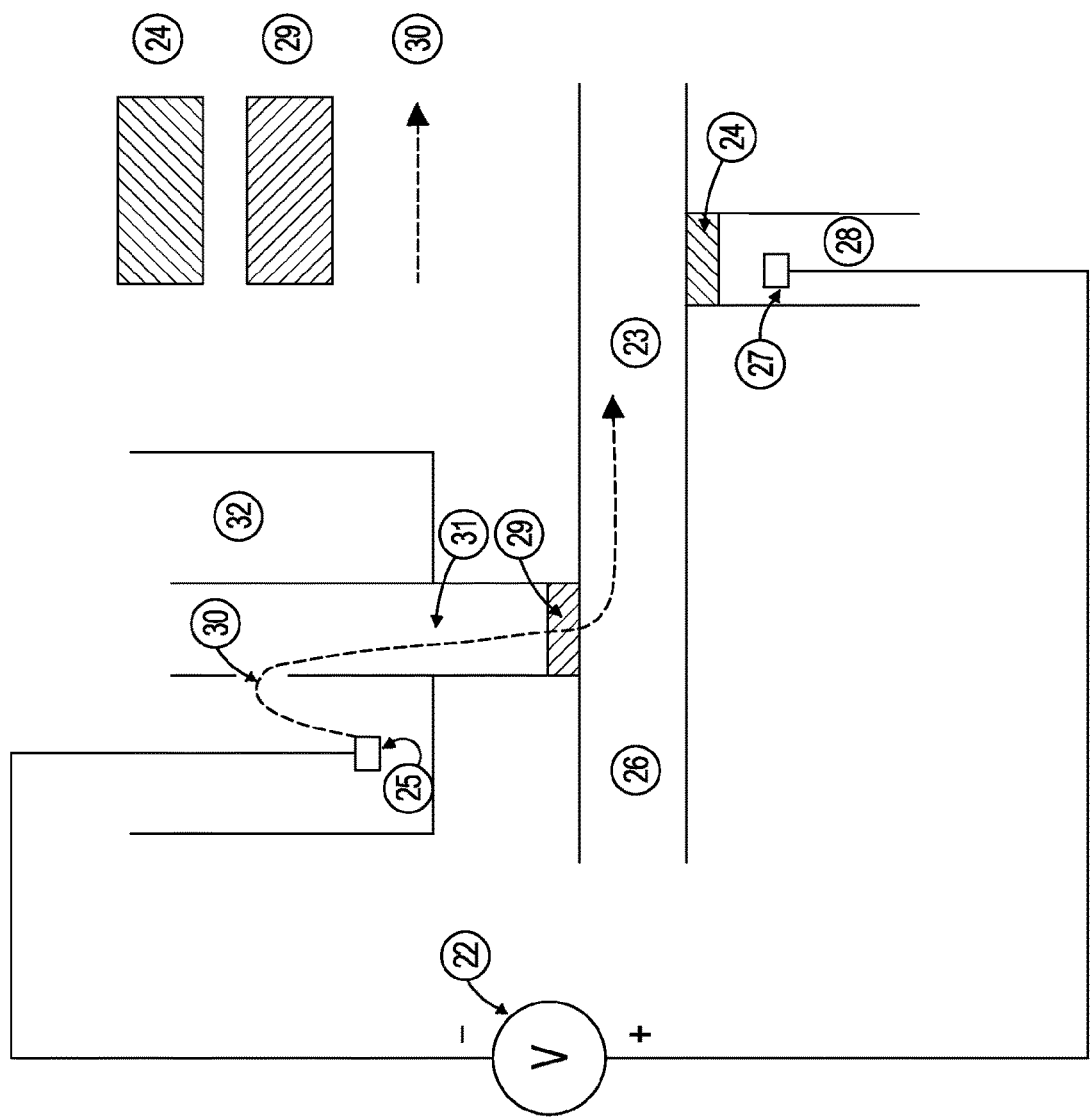
FIG. 26 is a schematic representation of one embodiment of a voltage diagram of the pre-treatment unit.

FIG. 26 shows the voltage diagram of one embodiment of the pre-treatment unit. One electrode (25) is placed in the electrolyte reservoir (32) and the other (27) in the CEM reservoir (28). The field (30) moves through the sample reservoir (31) and the filter layer (29) and into the fluidics channel (26). The CEM (24) creates a depletion zone that concentrates molecules in the fluidics channel prior to the CEM (23). The current (22) is capped at 0.8 mA and 200V. The system is run for sufficient time to move the molecules from the sample reservoir to point 23.

Figure 27:
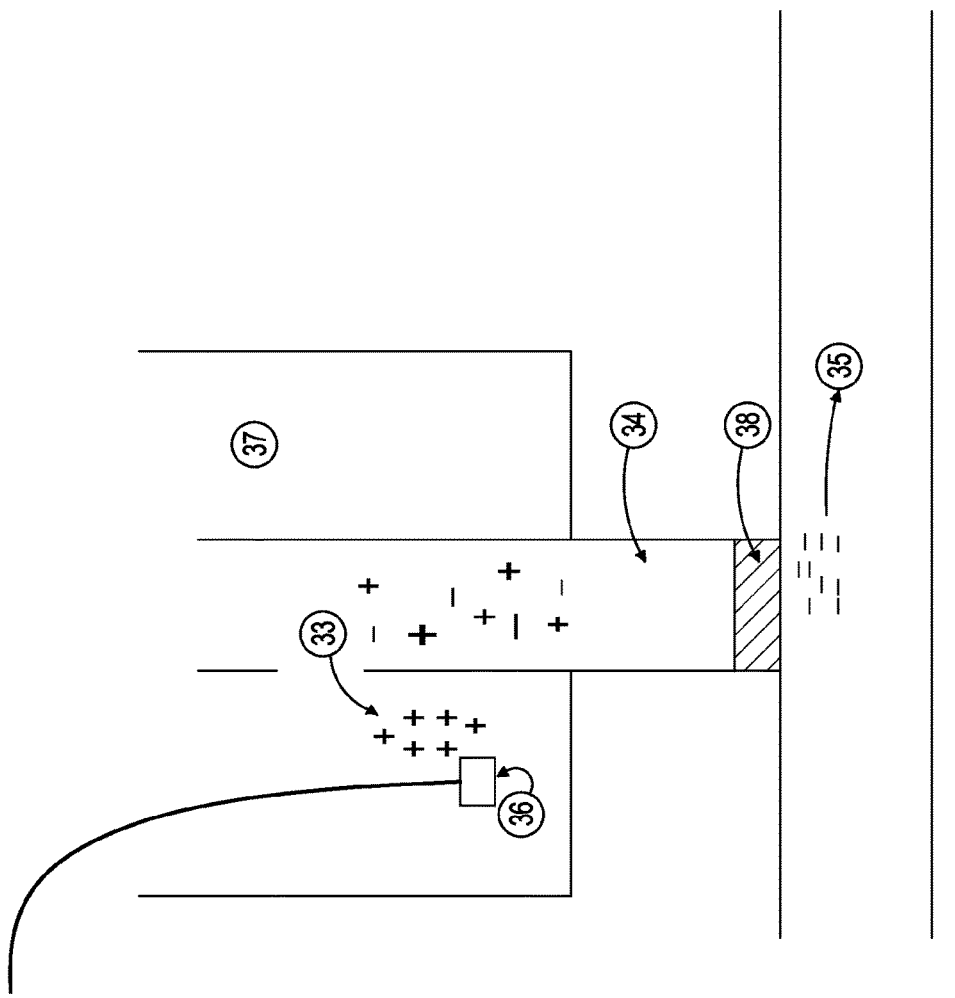
FIG. 27 shows the mixture of positive and negative molecules in the sample reservoir.

FIG. 27 shows the mixture of positive and negative molecules in the sample reservoir (34). The positive molecules (33) move toward the electrode (36). The negative molecules (35) move through the filter layer (38) into the fluidics channel.

The system is preferably used at room temperature. However, it will still function at lower temperatures, although the migration will be slower because it is more difficult for molecules to move through. On the other hand, if the temperature is excessively high, then mechanical stability breaks down. For example, porosity may change with temperature. For electrolytes, the higher the temperature the higher the conductivity. But at some point bubbles or evaporation may occur, or it may damage biomolecules. However, 37 C is likely a workable temperature because that is body temperature for these cells. In addition, it is also possible to isolate temperatures near the sensor and in other units/components of the chip to optimize the function.

In addition, the pH should be maintained. If the pH range is not maintained then the ability to sense and analyze the target is diminished or eliminated because the charge/attraction of the target molecule may be neutralized which prevents the electrical field from moving the target molecule from the sample reservoir through the filter gel and into the fluidics channel. Also, if the pH level is too high or low, the target molecules may be destroyed/damaged. A higher buffer concentration is needed with a higher applied current. A higher buffer concentration is also needed when current is applied for longer periods of time. The concentration must be sufficiently able to neutralize the O and H molecules generated with the current. Under conditions of a high current or longer period of time the current is applied or both, more O− and H+ molecules must be neutralized. Without neutralizing these molecules the pH level will change. It may be possible for a pH as low as 5-6 or as high as 9-10 though this is considered dangerous and a pH of 6-7 has been shown to be best able to protect DNA, maintain the proper charge/attraction, and best for sensing the target molecules.

In order to optimize the design of the pre-treatment unit, the application, sample size, sample type, and target molecule must be identified. The application will have specifications it requires including a level of accuracy (sensitivity and specificity), time to run the test, and a testing environment. The size of the sample is most critical to design optimization. The geometry, voltage, and filter layer are all affected by the sample size. Sample type may affect reactions with other materials, resistance to the current, and sample preparation (though sample preparation is a function of another unit to be designed and integrated). The target molecule will have a constant of "M" that affects the velocity of the molecule. Additionally, porosity in the filter layer (larger molecules=larger porosity) can be determined.

The pre-treatment unit is optimized for efficiency of molecular separation and filtration. Stable conditions within the unit, directed electrical field, force of the electrical field, surface charges of materials, prevention of electroosmotic flow, mechanical stability, and porosity are elements that change the efficiency of the pre-treatment unit.

Some embodiments of the integrated unit comprise two reservoirs, placement of electrode, holes in the sample reservoir, and a filter layer. The properties of the integrated unit include: the unit design must direct the electrical field to have an effect across all of the sample with the placement of the substrate; the three materials contained in the unit need to be in order and remain separate but in contact with each other, such that the electrolyte is on top, the sample solution in the middle, and the filter layer on the bottom and the substrate assists in keeping each layer separate, in sequence, and in contact; the placement of the electrode must allow for the electrical field to be directed to effect all of the sample; and the unit is designed for 100 μL of sample, optimization of geometry and mixtures of each fluid layer will vary with a change in the sample size.

In some embodiments of the pre-treatment unit, the agarose gel is 1 mm thick. However, there is a need to make it as thin as possible. This reduces the distance between electrodes and thus increases the efficiency of the electrical field. Also, it is a resistance for the molecules that pass through. But, too thin and the gel will break and ruin the function of the chip because there is not enough structural stability. It the geometry changes with the diameter of the opening, then thickness will need to be adjusted, thicker for wider, thicker for more current, thicker for more force of molecules. Function will still work with a lot more thickness, 5 mm. 8 mm. etc. but it will make the functionality slower. For instance from the 15 minutes currently to an hour or more.

In some embodiments of the pre-treatment unit, the electrolyte reservoir is designed as a reservoir of electrolyte fluid. The size, shape, and dimension may vary so long as there is sufficient area for the necessary volume of electrolyte liquid. The necessary area for a 100 μL sample is based on the applied current levels (see Liquid Electrolyte under Materials). More electrolytes will take more space and material but will not affect the chip function. Less electrolyte may by not be sufficient for the properties needed in the pre-concentration unit.

In some embodiments of the pre-treatment unit, the sample reservoir can be any shape. The dimensions can vary depending on sample size. Any changes in proximity of the sample to the filter gel will affect the overall process time of the chip. The closer the better. With a larger sample, the height or diameter or both could change to accommodate the volume. However, the distance between the electrode in the pre-treatment unit and the cation exchange tube will mean a change in current, volume required of electrolyte liquid, and overall process time for the chip. The sample reservoir is designed to contain the sample below the electrolyte fluid. The sample reservoir is also designed with a 'beveled' bottom that allows for the filter gel to have greater stability. Dimensions are 3 mm at opening. However, the height and diameter affect the distance the current must travel and the height and diameter also affect the ability to direct the electrical field, such that a wider diameter may cause some of the sample and the molecules to be outside the area of the electrical field, at least where there is sufficient force.

In some embodiments of the pre-treatment unit, the electrode is placed inside the electrolyte reservoir below the hole that opens into the sample reservoir. This helps direct the electric field up into the sample reservoir so that the field will encompass as much of the sample as possible. It is possible to place the electrode above the sample or various locations around the electrolyte reservoir with similar effects. Placing the electrode above the opening may weaken or miss-direct the electrical field. The effects of electrode placement are larger with a larger sample and/or sample reservoir.

In some embodiments of the pre-treatment unit, the distance between the electrode in the pre-concentration unit and the cation tube effects the velocity and efficiency of the electric field. The electric field moves the target molecules through the filter gel and into the fluidics channel and then on towards the sensor. If the distance is changed because of additional height and/or diameter in the sample reservoir to accommodate a larger sample or other reasons, then the efficiency suffers. The current must be adjusted (higher for more volume) and the placement of the electrode may need adjustment so that the electric field affects the entire sample.

Applications

The pre-treatment unit disclosed herein has various applications and implementations that can readily be ascertained by one of skill in the art. The unit may be used, for example, for the separation, filtration, concentration, isolation, and controlled movement of targeted macromolecules. This unit is useful in the preparation of biological samples for detection. In addition, this system has been shown to prepare liquids by eliminating or adding macromolecules, ions, and other elements. The system controls the movement and placement of macromolecules by controlling and manipulating phenomena associated with electrical force.

The pre-treatment unit separates molecules, including proteins, nucleotides of varying length, and molecules of either positive or negative charges. Molecules are targeted by their charge and separated, filtered, and moved from one reservoir to another divided by a filter layer. This technology also filters molecules by size. Sample can be of varying types of biological samples that include, but are not limited to blood, saliva, stool, urine, tissue, etc. Additionally, the sample can be any prepared sample from any process.

The pre-treatment unit prepares samples for biosensing by preprocessing molecules and isolating them from other debris or material. Additional uses for the pre-treatment unit may include: separation of macromolecules—macromolecules are separated based on charge, negative or positive, from macromolecules of a different charge, negative or positive, so that the like charged macromolecules move to another reservoir apart from those differently charged molecules; filtration of macromolecules—the size of the porosity of the filter layer prevents like charged macromolecules greater in size than the pores, such that by design molecules may be targeted by size and filtered by size; movement of macromolecule—macromolecules are moved such that by design the targeted macromolecules are controlled in the direction and speed of their movement to desired locations; concentration of macromolecules—the targeted macromolecules are concentrated and held in a specific area/location based on the need and design; applicable for isolation, detection, measurement, research, etc. of any charged macromolecule; and purification, mixing/purifying liquids (such as deionized water, dyes, pollutants).

Pump Unit

The pump unit disclosed herein provides flow to the integrated chip. This unit can be integrated into the control unit or integrated into the integrated chip. The pump provides fluids to prime the integrated chip and establish appropriate conditions for the electrical fields and detection. Additionally, the washing steps for the sensor unit are provided by the pump unit.

The ability of microfluidic biochips to control fluid flow offers advantages such that 1) molecular diffusion limitations are reduced by delivering the target nucleic acid underneath the sensor, thus increasing the hybridization efficiency to the complementary probes; and 2) the shear force exerted by the flowing fluid removes non-specifically bound molecules. This has been demonstrated by pumping a buffer solution containing kb-long ssDNA at a high flow rate (up to 100 μl/min) across sensors functionalized with a short 26 base-long oligoprobes complementary to a middle segment of the kb-long target ssDNA (Senapati 2009, Basuray 2009, Cheng 2010). The rapid convection by the flow reduces the assay time from hours to minutes by reducing diffusion limitations.

Additionally, continuous flow significantly enhanced specificity such that one mismatch (e.g., a single nucleotide polymorphism) in a 26 pair segment of the kb target was discriminated against a perfectly matched target (Cheng 2010). Moreover, a nanomembrane-based pre-concentration unit (described later) will be placed adjacent to the sensor to rapidly trap and concentrate the target nucleic acid molecules and detect the hybridization event of target with the specific oligoprobes functionalized on the sensing membrane.

Figure 28:
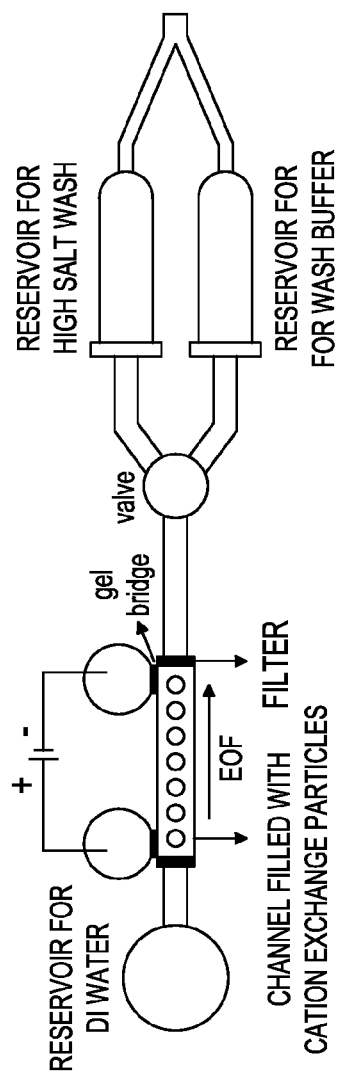
FIG. 28 shows one embodiment of the pump system, designed to have no mechanical operation, only electrical operation and wherein the use of highly charged particles increase the efficiency of the pump as a function of $F_{e1}=QE$.

One embodiment of the pump unit is depicted in FIG. 28, and is designed to have no mechanical operation, only electrical operation. In the channel the substrate has a layer of functional groups. The contra ions are in the channel that can freely move. The H ions will be dispersed (with water) in close vicinity of the substrate with a higher concentration towards the substrate and less in the center of the channel. If a DC filed is applied then the contra-ions will feel the force and will be pulled towards the electrode, the positive in one direction and the negative in another direction. There is a preferential direction of movement. The rest of the solution will feel the force and will move along with it. The whole electrolyte will move in a single direction. The more charges fixed to the wall the better the pump.

If the channel is filled with ions that this makes the pump more efficient. But, after time in a high electrical field the ions degrade. Thus, there is a limit to the field that can be applied. Excess current is needed to have enough force to pump the buffers in the integrated chip for the capabilities of this design.

Because of the limitations of the electroosmotic pump, a valve and syringe system was used for PBS solution at various concentrations in the integrated unit. The pump unit applies flow, pressure, and controls washing fluids.

Integrated Chip

FIG. 2 shows a block diagram of the functional overview of the integrated chip. The pre-treatment unit filters, transports, localizes, and concentrates molecules. These molecules are then transported and concentrated by the pre-treatment unit. Finally, the sensor detects the molecules. Fluids are inserted into the fluid inlet and the fluid is collected at the fluid waste after moving through the integrated chip.

In some embodiments of the integrated chip, a CEM and channel are integrated into the chip to lyse the cells. A high electrical field is used to lyse the cells and then filter debris before moving the remaining DNA into the channel toward the sensor. This is limited because too many cells will clog the filter and will back up the system with too much pressure. Also, it is difficult to get the correct field to break the cells, especially because the field varies across the channel. Also, the CEM creates a depletion zone and blocks the molecules through some degree. It would take a lot of balancing the field (and its blocking effect) and the lysing of the cells.

Figure 29:
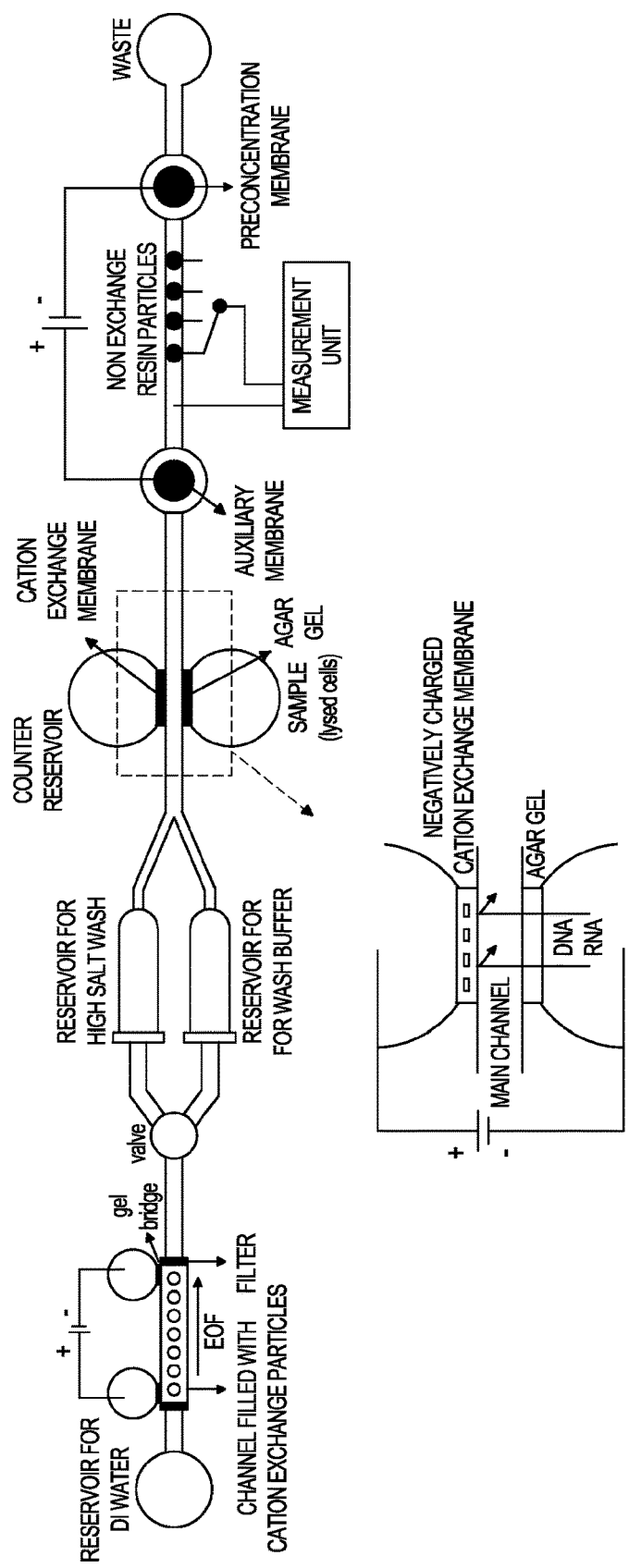
FIG. 29 is a side view representation of one embodiment of the integrated chip, which integrates the pre-treatment unit, the pre-concentration unit, and the sensor unit. This embodiment also shows the integration of the pump with the other components as the total design fully runs by only electricity.

FIG. 29 shows an integration of the EOF pump with the other components as a total design fully run by only electricity. Each of the units was worked on independently at first and is discussed previously. The pump was removed and replaced with the valve system.

In one embodiment of the integrated chip, the chip is fabricated with a combination of PMMA for making microfluidic channels and casting for embedding functional elements (membranes/particles/gels). The platform allows the use of both membrane and granule sensor which are embedded within a screw. The platform can be readily adopted for a wide range of applications with minor customization.

In some embodiments of the integrated chip, the reference electrode opening is placed after the sensor. Also, the CEMs are placed closer together and after the sensor. The depletion region was calibrated to be under the AEM. Thus, no openings exist between the filter layer of the pre-treatment unit and the sensor unit, resulting in a very high capture of the target molecules.

In some embodiments, the integrated chip system can be effectively used for separation of different species as long as these two different species have different electrophoretic mobility. Different species are located at different positions along the channel based on the strength of the electrical field.

The combination of these components (pre-treatment, pre-concentration, and sensing units) have been arranged together on a chip that, when properly automated, permits the whole testing procedure to be concluded without any manual external manipulation. Pipette tapes, membranes, tubings, resin, glues, and other means have been used to implement the inventions herein. The result is a very low cost system.

The method of using the chip comprises: providing an integrated chip, loading a test sample into the pre-treatment unit, establishing a stable baseline for the sensor, and obtaining a first measurement. After the first measurement is obtained, the method further comprises applying a DC field on the pre-treatment unit, extracting all the negatively charged molecules from the pre-treatment unit, localizing the charged molecules at the sensor. In some embodiments, the method further comprises bringing the other molecules from the channel to this region to improve the specificity or selectivity or sensitivity, washing nonspecific molecules from the sensor, and obtaining a second measurement of the membrane sensor.

The analysis of the measurements results in the determination that either there is no target, wherein the curve is identical to the baseline or there was a target and a difference between the baseline and sample curve is observed.

Furthermore, the concentration of the target can be estimated from the shift in the tops of the baseline and target CVC.

A non-target, or nonspecific target, could be, for example, a single strand and a complete mismatch from the target probe, resulting in no change to the membrane sensor. On the other hand, a target, which in some embodiment could be, for example, microRNA from oral cancer, a change is detected, wherein the change can be used to quantitate the amount of target molecule.

As described herein, each unit of the integrated chip can be used as a standalone unit. The pre-treatment unit may be used for the isolation of nucleic acids. One application, for example, is the need to recover a bend from gel electrophoresis. The pre-concentration unit can be used to pre-concentrate the molecules in the chip, resulting in a sample with very high concentrations with a high ionic strength.

Additionally, the whole integrated chip can be utilized to perform a complete test, with the use of the concept of PCR amplification and membrane detection or an alternative concept which is based pre-treatment, pre-concentration, and specific detection.

This chip can be used with an instrument that allows all the measurement automatically. The chip can also be used to do multi-target detection. Examples include, but not limited to, multiple microRNAs for oral cancer detection or dengue, pancreatic cancer, bladder cancer, or breast cancer.

Structure & Method

The integrated microfluidic membrane sensing technology disclosed herein is an automated process for separating target nucleic acids of genetic material. This includes microRNA (miRNA), RNA, and DNA or chains of nucleic acids of varying length. This involves various units that contribute to the separation, manipulation, concentration, and analysis of the target molecules.

The process steps for one embodiment of the invention:
1. System washed & primed from buffer reservoir into Inlet and through system until no air bubbles and system full of buffer (>0.5 mL 0.1×PBS)
2. Baseline measurement with step up current with initial load of 0.0 mA, scan rate of 1.E−006 mA/second, to a final load of 3.E−005 mA with measurements every 0.5 seconds (total time 30 seconds and 60 data points), I-V curve is measured and recorded
3. A second wash similar to step 1 (0.5 mL w/0.1×PBS)
4. A second I-V curve measurement (repeat step 2)
5. A third wash (Repeat step 3)
6. A third I-V curve measurement (repeat step 2)
7. Display all I-V curves to verify they overlap, this means chip and sensor are ready
8. Apply DC current with 202V in yellow V limited to 0.8 mA for 15 minutes
9. (this step may not be needed) Switch to orange V applying 100-150V limited to 0.8 mA and wash system
10. Wash system with high then low concentrations of buffer (0.5 mL w/4×PBS then w/0.1×PBS)
11. Take I-V curve measurements (repeat step 2) and record
12. Repeat step 3 (0.5 w/0.1×PBS)
13. Repeat step 11
14. Continue steps 12 & 13 until first section of I-V curve overlaps with those in steps 2, 4, & 6
15. Measure shift in I-V curve
16. Algorithm determines quantity of target, presence of target (in the future the ratio of the target to another reference target; three possible determinations: 1-If target present, 2-Quantity of target, 3-Ratio or relative quantity of target)
17. Algorithm determines presence of cancer, virus, etc. and delivers report Note: For multiple probe sensor units, steps 2-6 and 10-15 may be completed for each probe in the unit in a sequential or parallel manner.

Electrolyte buffer is pumped from the buffer reservoir through the inlet into the fluidics channel. All air bubbles and potential debris are washed from chip into the waste reservoir.

A current source gradually increases the amps in a step up process through electrode in each sensor unit and the measurement electrode reservoir. The step up is set to increase at 1 mA per second to a target of 30 mA. The total time takes 30 seconds per sensor. Reference electrodes in each sensor and in the reference electrode reservoir measure the change in voltage across each sensor. Software records the changes. The process is repeated three times for each sensor for a total of 1.5 minutes per sensor. The recorded baseline becomes the reference point to measure any change during detection. The current step up process is controlled by the same software that records the changes. After the measurement the current is turned off.

A current is applied from the voltmeter through the negative electrode in the pre-treatment unit and the positive electrode in the concentration unit. This is a constant of ~200V (0.8 A). After about 15 minutes, 95% of the target molecules at a femtomolar concentration have been concentrated near the sensor and hybridization has taken place. The current stops after the desired time.

A higher concentration of buffer solution is pumped through the fluidics channel from the buffer reservoir to wash the system. Then the original buffer concentration is pumped back into the system to restore the original environment to the pre-baseline measurement conditions.

The baseline measurement process is repeated exactly as before. The shift in the curve generated is measured. The amount of the shift is correlated to the quantity of the target molecule.

Capabilities

The integrated chip realizes short run times with a total time of 19-23 minutes; 2-3 minutes for steps 1-7, 15 minutes step 8, 2-5 minutes steps 9-17, Potential for <15 minutes total following optimization. Sensitivity of femtomolar in 100 μL, sample (greater sensitivity in larger sample). Specificity of 2 in 26 base pairs (limits of PCR are very similar according to Zdenek). Finally, single probe sensor unit shown to detect miRNA, RNA, DNA, *e coli*, dengue, and spiked miRNA targets.

When integrated into microfluidic chips, ion-selective nanoporous polymer and solid-state membranes can be used for on-chip pumping, pH actuation, analyte concentration, molecular separation, reactive mixing, and molecular sensing. They offer numerous functionalities and are hence superior to paper-based devices for point-of-care biochips, with only slightly more investment in fabrication and material costs required. In this review, the inventors first discuss the fundamentals of several nonequilibrium ion current phenomena associated with ion-selective membranes, many of them revealed by studies with fabricated single nanochannels/nanopores. The inventors then focus on how the plethora of phenomena has been applied for transport, separation, concentration, and detection of biomolecules on biochips.

Sample Preparation

There are four elements necessary to prepare the sample for use in the integrated chip: 1) sample—could be blood, serum, urine, mucus, tissue or any material taken from the body, plant, organic material; 2) lysis of cells—access to target molecules inside of cells, exosomes, or other items containing the target molecules; 3) dilution of sample—allows for separation and movement; and 4) means of suspending the sample—solution must be between the electrolyte fluid and the filter gel in the pretreatment unit.

Control Unit

FIG. 2 shows the units and components of the system. A control unit houses the pump system, voltage/current source, analysis/results output, and the programmable controller. These automate the functions of the integrated chip. The sample is inserted into the integrated chip. The control unit automates all functions of the integrated chip. The integrated chip is a disposable unit that is inserted into the control unit.

For a typical experiment, finger-pricked blood sample will be drawn into a capillary and delivered to the sample pre-treatment unit. After initial delivery of the sample, the user will press a button on the diagnostic instrument to carry out all the steps automatically. The automated platform will then lyse the virus (if any), transport and concentrate the nucleic acids and finally detect it using the nanomembrane sensor using the methods and units as described previously.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A system for detecting target biomolecules in a sample, the system comprising:
    a control unit, comprising:
        a pumping system comprising at least one pump fluidly coupled to a fluidics system comprising at least one fluidic channel, wherein the at least one pump is configured to generate fluid pressure and flow within the fluidics system;
        a voltage-current source;
        an analysis-output module; and
        a programmable controller, operably coupled to and configured to control the pumping system, the voltage-current source, and the analysis-output module; and
    an integrated chip configured to insert reversibly into the control unit, and fluidly coupled to the pumping system, electrically coupled to the voltage-current source, and operably coupled to the analysis-output module, wherein the integrated chip comprises:
        a pre-treatment unit, comprising a fluid inlet in fluid communication with the pumping system, and a sample inlet, wherein the pre-treatment unit comprises a pre-treatment fluidic channel, at least two electrodes coupled to the voltage-current source and configured to generate an electric field within the pre-treatment fluidic channel, and a molecular filter within the pre-treatment fluidic channel, such that sample molecules flowing through the pre-treatment fluidic channel are separated by both charge and by molecular weight;
        a pre-concentration unit, comprising at least two ion exchange membranes disposed along a pre-concentration fluidic channel, and at least two electrodes coupled to the voltage-current source and configured to generate an electric field within the pre-concentration fluidic channel, wherein the pre-concentration fluidic channel is fluidly coupled to the pre-treatment fluidic channel and the pumping system, such that sample molecules are concentrated within the pre-concentration fluidic channel at a location where opposing flow and electrophoretic forces are substantially equivalent; and
        a sensor unit comprising an ion exchange membrane disposed between first and second fluidic channels, wherein one of the fluidic channels is fluidly coupled to the pre-concentration fluidic channel and the pumping system, wherein the ion exchange membrane is functionalized with a probe complementary to the target biomolecule, and a first pair of opposing electrodes positioned within the first and second fluidic channels on opposite sides of the ion exchange membrane, wherein the first pair of opposing electrodes are configured to apply an input signal across the ion exchange membrane, and a second pair of opposing electrodes positioned within the first and second fluidic channels on opposite sides of the ion exchange membrane, wherein the second pair of opposing electrodes are configured to measure an output signal.

2. The system of claim 1, wherein the fluidic system further comprises at least one fluid reservoir and at least one waste reservoir.

3. The system of claim 1, wherein the at least one pump comprises an electroosmotic pump, a valve and syringe system, or both an electroosmotic pump and a valve and syringe system.

4. The system of claim 1, wherein the molecular filter in the pre-treatment unit comprises a nanofilter, a hydrogel, or a nanofilter and a hydrogel.

5. The system of claim 1, wherein the pre-treatment unit further comprises a cation exchange membrane disposed along the pre-treatment fluidic channel.

6. A method for quantifying the presence of a target biomolecule in a sample, the method comprising:
    introducing the sample to an integrated membrane sensor via a sample inlet;
    flowing the sample through a pre-treatment fluidic channel comprising a molecular filter and at least two electrodes coupled to a voltage-current source and configured to generate an electric field within the pre-treatment fluidic channel, wherein target biomolecules in the sample are separated from other biomolecules by both charge and by molecular weight;
    flowing the separated target biomolecules through a pre-concentration fluidic channel, comprising at least two cation exchange membranes disposed along the pre-concentration fluidic channel, and at least two electrodes coupled to a voltage-current source and configured to generate an electric field within the pre-concentration fluidic channel, wherein target biomolecules are concentrated within the pre-concentration fluidic channel at a location where opposing flow and electrophoretic forces are substantially equivalent;
    flowing the concentrated target biomolecules through one of a pair of fluidic channels separated from one another by an ion exchange nanomembrane, wherein the nanomembrane is functionalized with a probe configured to bind the target biomolecule, and wherein the nanomembrane and the target biomolecule are oppositely charged;
    applying limiting and overlimiting current across the nanomembrane; and
    detecting a change in electrical potential across the nanomembrane, wherein the change in electrical potential is related to the target biomolecule binding to the probe, thereby quantifying the presence of the target biomolecule.

7. The method of claim 6, further comprising providing an AC sinusoidal electromagnetic perturbation while detecting the change in electrical potential across the nanomembrane.

* * * * *